(12) United States Patent
Polidoro

(10) Patent No.: US 11,291,743 B2
(45) Date of Patent: Apr. 5, 2022

(54) CEILING-MOUNTED DECONTAMINATION UNIT WITH LUMINAIRE

(71) Applicant: John Polidoro, Bensalem, PA (US)

(72) Inventor: John Polidoro, Bensalem, PA (US)

(*) Notice: Subject to any disclaimer, the term of this patent is extended or adjusted under 35 U.S.C. 154(b) by 0 days.

(21) Appl. No.: 16/855,374

(22) Filed: Apr. 22, 2020

(65) Prior Publication Data
US 2020/0289698 A1 Sep. 17, 2020

Related U.S. Application Data

(63) Continuation-in-part of application No. 15/589,548, filed on May 8, 2017, now Pat. No. 10,808,964.
(Continued)

(51) Int. Cl.
| | |
|---|---|
| *A61L 9/20* | (2006.01) |
| *F21S 8/02* | (2006.01) |
| *F21V 33/00* | (2006.01) |
| *F21V 21/03* | (2006.01) |
| *F21S 8/04* | (2006.01) |
| *F21V 21/04* | (2006.01) |
| *F21V 1/04* | (2006.01) |
| *F21Y 115/10* | (2016.01) |

(52) U.S. Cl.
CPC ............... *A61L 9/20* (2013.01); *F21S 8/026* (2013.01); *F21S 8/04* (2013.01); *F21V 21/03* (2013.01); *F21V 21/04* (2013.01); *F21V 33/0064* (2013.01); *A61L 2209/12* (2013.01); *A61L 2209/15* (2013.01); *F21Y 2115/10* (2016.08)

(58) Field of Classification Search
CPC .... A61L 9/20; A61L 2209/15; A61L 2209/12; A61L 2209/111; A61L 2209/212; A61L 9/015; F21S 8/026; F21S 8/04; F21V 21/04; F21V 33/0064; F21V 21/03; F21V 33/0088; F21Y 2115/10; F21Y 2105/10
See application file for complete search history.

(56) References Cited

U.S. PATENT DOCUMENTS 3,674,421 A * 7/1972 Decupper ................. A61L 9/20
  422/121
3,846,072 A * 11/1974 Patterson ................. F24F 3/16
  96/222
(Continued)

*Primary Examiner* — Tsion Tumebo
(74) *Attorney, Agent, or Firm* — Law Offices of Leo Mikityanskiy, P.C.; Leonid Mikityanskiy

(57) ABSTRACT

A ceiling-mounted decontamination unit with one or more internal decontamination sources, which may be UV-C emitters, inside a housing with a hingable panel for access to the internal space of the housing for maintenance and repairs, and one or more fans inside the housing that re-circulate the air in a room and subject the air to the germicidal internal decontamination source inside the housing, decontaminating the air passing through the ceiling-mounted decontamination unit's internal space and destroying viruses, bacteria, and other pathogens. The ceiling-mounted decontamination unit draws the air in from the room or area where the ceiling-mounted unit is installed, subjects the air to the internal decontamination source destroying pathogens, and returns the decontaminated air back to the same room or area from which the air is drawn. An optional luminaire or external decontamination source may be attached to the room- or area-facing exterior of the ceiling-mounted decontamination unit.

11 Claims, 23 Drawing Sheets

Related U.S. Application Data

(60) Provisional application No. 62/990,937, filed on Mar. 17, 2020, provisional application No. 62/836,877, filed on Apr. 22, 2019, provisional application No. 62/391,681, filed on May 9, 2016.

(56) References Cited

U.S. PATENT DOCUMENTS

| | | | |
|---|---|---|---|
| 4,553,992 A | 11/1985 | Boissinot et al. | |
| 4,786,812 A * | 11/1988 | Humphreys | A61L 9/20 250/455.11 |
| 5,225,167 A | 7/1993 | Wetzel | |
| 5,523,057 A * | 6/1996 | Mazzilli | A61L 9/20 250/436 |
| 5,891,399 A * | 4/1999 | Owesen | A61L 9/20 422/121 |
| 6,062,977 A | 5/2000 | Hague | |
| 6,500,387 B1 * | 12/2002 | Bigelow | A61L 9/20 250/432 R |
| 6,619,063 B1 | 9/2003 | Brumett | |
| 6,855,295 B2 * | 2/2005 | Kulp | F24F 1/0071 422/121 |
| 7,251,953 B2 | 8/2007 | Wetzel et al. | |
| 8,350,228 B2 | 1/2013 | Welker | |
| 8,398,264 B2 | 3/2013 | Anderson et al. | |
| 8,439,517 B2 | 5/2013 | Welker | |
| 8,702,264 B1 * | 4/2014 | Rashidi | F21S 8/026 362/147 |
| 9,517,280 B2 | 12/2016 | Lynn et al. | |
| 2003/0217641 A1 | 11/2003 | Palestro et al. | |
| 2006/0213157 A1 | 9/2006 | Kalous et al. | |
| 2009/0211284 A1 * | 8/2009 | Yabu | F24F 1/0073 62/259.1 |
| 2015/0338084 A1 * | 11/2015 | Ryder | F21V 3/04 362/606 |
| 2016/0138789 A1 * | 5/2016 | Brown | F21V 23/0442 362/95 |
| 2019/0170341 A1 * | 6/2019 | Lax | F21V 3/04 |
| 2019/0292315 A1 * | 9/2019 | Niemiec | A61L 9/20 |

\* cited by examiner

CEILING-MOUNTED DECONTAMINATION UNIT WITH LUMINAIRE

This patent application is a nonprovisional patent application of and claims priority from the provisional patent application Ser. No. 62/836,877 filed on Apr. 22, 2019, and also claims the benefit of the provisional patent application Ser. No. 62/990,937 filed on Mar. 17, 2020 and the nonprovisional patent application Ser. No. 15/589,548 filed on May 8, 2017, which claims benefit of the provisional patent application Ser. No. 62/391,681 filed on May 9, 2016, all of which are hereby incorporated by reference in their entirety. The disclosures, drawings, abstracts, and claims of these patent applications, all of which are attributed to the Applicant, will be helpful in understanding the present invention.

This invention was not made pursuant to any federally-sponsored research and/or development.

THE FIELD OF INVENTION

Dangerous bacteria, viruses, and other pathogens are present in the air and on various physical surfaces, which are easily spread through air and by contact with contaminated surfaces. Certain pathogens, bacteria, and viruses are airborne, easily inhaled, and can travel quickly from person to person as well as settle on room surfaces. These airborne or surface pathogens can cause infections, illness and even death to individuals who come in contact with these pathogens.

Methods of control are difficult and labor intensive, involving washing or wiping surfaces with caustic germicidal substances, leaving a film and/or smell of these substances on surfaces. An even greater problem was disinfecting the air to destroy airborne bacteria and other pathogens that could resettle on surfaces. Fast spreading viruses and other airborne pathogens are capable of settling onto room objects and re-contaminating surfaces immediately after the surfaces are physically cleaned and disinfected making it extremely difficult to maintain a safe, healthy, and germ/virus/pathogen-free environment.

The present invention relates to a self-contained air decontamination system, intended to install directly into or onto a ceiling in a room, in a non-movable or repositioning relationship, designed to destroy pathogens in the air drawn into the system and return decontaminated air back into the room directly from the unit. Further, present disclosure relates to a device that includes additional components designed to mount to the system such as ceiling tile in frame, room luminaire, and room surface and air decontamination luminaire in a hingable, removable, replaceable, and interchangeable.

BACKGROUND OF THE INVENTION

The benefits of devices that use ultraviolet spectrum light for killing bacteria and other pathogens are known in the art. Non-visible, Ultraviolet C or Germicidal light source technology is known to destroy the DNA or ability of viruses, bacteria, and other pathogens to reproduce. Visible light utilized on common light fixtures used as a light source is usually in the 400-700 nm range. UV light used to destroy viruses, bacteria, and other types of pathogens are typically below 400 nm (although any light below 400 nm is considered UV light). Some of the methods of using UV light for killing viruses, bacteria, and other pathogens are disclosed in U.S. Pat. No. 8,350,228 (Welker), the disclosure of which is incorporated herein by reference. However, Welker discloses an extremely heavy unit that requires disengagement from the mounting surface to pivot 90 degrees, below ceiling surface, for service or maintenance in a manner which is unsafe and may cause the unit to break free from its attachment means. The Welker unit breaking fee may injure the service technician or maintenance person, disconnect from the Install Apparatus (custom brackets required in Welker) and power supply connection, or cause damage to the installation facility. The complete germicidal unit of Welker is designed to disengage from ceiling to swing downward to allow access to the top of the unit to change the germicidal source. The combination of the Welker's unit weight along with the weight of the exiting troffer housing create a situation that may exceed the maximum weight for ceiling grid specifications designed to support a much lighter, standard troffer unit alone.

The current global crisis creates a new environment of exposure that requires greater need for decontamination systems. Existing facilities may not be suited to add additional germicidal devices to their installed ceiling systems due to lack of available space, congestion, or other items occupying the space required to install additional systems. There is a need to improve the quality of air including the decontamination of airborne microorganisms and pathogens in the air we breathe.

Air filters and other air processing systems involve ductwork or existing HVAC Systems that draw air into the facility HVAC System for processing. These systems are limited to larger ceiling duct systems where effective, where the HVAC air return duct is located and may not be capable of decontaminating office or hospital area distant from the return ducts. Poor efficiency will also result from offices or hospital rooms where doors are closed, making importing the room air into the return duct difficult or impossible. Facilities that include wall-installed HVAC ductwork are inefficient due to the return duct location at the perimeter of the room.

An essential element of quality air decontamination in a room requires a centrally located system capable of importing room air in an equal manner that assures a balanced and efficient process. This involves the use of facility ceiling or ceiling structures to position air decontamination systems in locations that can perform effectively. Positioning an air decontamination system in the optimal location may not always be possible in many facilities due to the lack of available space in the ceiling or in the ceiling recessed grid system. HVAC ductwork, lighting fixtures, electrical wiring, plumbing, computer wiring, joists and beams, and other objects limit the available area to install a new air decontamination system.

Most offices and hospital facilities have recessed or drop ceiling, also referred to as T-Bar, Inverted T-Bar, or grid ceiling, for aesthetic reasons in order to accommodate the various elements typically associated with a ceiling structure (wires, ducts, pipes, beams, etc.). Recessed drop ceilings also reduce the size of a room cavity by lowering the ceiling which reduces the cost associated with heating or cooling a facility.

Since HVAC system return ducts are not positioned in ideal locations and available space is limited in most recessed drop ceilings, the ideal location for an efficient room air decontamination system would be in the available space in the ceiling or in the space occupied by existing room luminaires.

Installing an air decontamination system into a centrally-located open space in a recessed drop ceiling would provide the most efficient system for air decontamination. Many offices and hospitals with recessed drop ceilings have recessed luminaires equally spaced in the ceiling grid. This often allows for several ceiling tiles be positioned between the installed luminaires. Depending on the ceiling grid pattern and location of the installed luminaires, an available space on the recessed ceiling grid that is occupied only by a ceiling tile would be an ideal location to install an air decontamination system.

What is needed is a ceiling-mounted decontamination unit, permanently mounted into the ceiling, which efficiently decontaminates the air passing (circulating) through the decontamination system to destroy the bacteria, viruses and other pathogens in the air and allows easy access to all components for maintenance and repair from the room side of the unit without disengaging the system from the ceiling grid. The unit should also be capable of replacing a recessed drop ceiling tile or recessed grid luminaire with an air decontamination system that is safe, effective, and user friendly offering fast and efficient maintenance for facilities where closing a room for maintenance is a challenge and costly.

The present invention solves this problem by providing a ceiling-mounted decontamination unit with luminaire, which the Applicant also refers to as a Recessed Ceiling or Surface Mounted Decontamination System, that draws in air from room or area, subjects the air in the unit to a decontamination source destroying harmful viruses, bacteria, and other pathogens, and re-circulates or returns the decontaminated air directly back to the same room or area. The present invention relates more particularly to a system and device that includes one or more UV-C emitters inside the housing, and one or more fans inside the housing that re-circulate the air in a room and subject the air to the germicidal decontamination source inside the housing, thereby decontaminating the air passing through the ceiling-mounted decontamination unit internal space and destroying viruses, bacteria, and other pathogens.

This ceiling-mounted decontamination unit includes a hingable frame, preferably with a latch, for grid ceiling tile to allow facilities to match existing ceiling type. The hingable frame allows a common recessed ceiling tile to be inserted into the hingable frame for easy attachment to the Recessed Ceiling and Surface Mounted Germicidal Decontamination System's hinge and latch provision.

However, the system can also incorporate a recessed grid ceiling luminaire, or room luminaire, to provide an air decontamination system along with a recessed luminaire capable of illuminating a room and being installed into the ceiling-mounted decontamination unit's hinge and latch provision.

In addition, in areas of higher concern with greater pathogen contamination, the system may incorporate a hinged Room Surface and Air Decontamination Luminaire into the ceiling-mounted decontamination unit's hinge and latch provision to decontaminate surfaces and air in a room. The hinged Room Surface and Air Decontamination System includes a decontamination source mounted on the surface of the Room Surface and Air Decontamination System exterior surface to make direct contact with the surfaces and air in a room. Similar to the Hinged Ceiling Tile in frame and the Hinged Room Luminaire, the Hinged Room Surface and Air Decontamination Luminaire is designed to hinge or open downwardly, toward the floor, to allow access to the maintenance panel on the air decontamination chamber for maintenance and repairs.

The components associated with the air decontamination system should accessible from below the installed unit on the ceiling grid. Access to the decontamination source, power supply connection, filer, drivers, ballasts, means for moving air, and all other components are available from below the installed unit, on the room side of the installed unit, and without moving or disengaging the air decontamination system from the installed position on the ceiling grid.

Installing an air decontamination system may require the removal of an existing luminaire from the recessed drop ceiling or other ceiling type. The device incorporates provisions to install or attach a room luminaire directly onto the housing of the air decontamination system that does not alter the performance of the air decontamination process. The system includes a hinge and latch provision designed to allow the attachment of a room luminaire that will illuminate the room as effectively as the removed luminaire. The hinge and latch feature combined with a custom-size luminaire is designed to install onto the front surface of the air decontamination system, preferably between the air decontamination air processing features.

In areas of greater pathogen contamination, the air decontamination system includes provisions to install or attach a room surface and air decontamination luminaire directly onto the air decontamination system that does not alter the performance of the air decontamination process. The system includes a hinge and latch provision designed to allow the attachment of a room surface and air decontamination luminaire that will effectively destroy pathogens on the surfaces and air in room where installed. Safety features are incorporated into the room surface and air decontamination luminaire decontamination sources. The hinge and latch features combined with a custom-size room surface and air decontamination luminaire is designed to install onto the air decontamination system, preferably between the air decontamination air processing features.

LIGHT FIXTURE. The light fixture or room luminaire design is completely self-contained with all lighting required components attached or secured to the room luminaire. The room luminaire is dependent on the ceiling-mounted decontamination unit as a means of installation with provisions for attachment, hinging or pivoting, latch or securing device, and power supply means. When installed, the attached light fixture or room luminaire has no direct association with the Recessed Ceiling or Surface Decontamination System decontamination process but does provide a quality substitute or replacement light source when an existing light fixture is removed from the grid ceiling or other ceiling.

SUMMARY OF THE INVENTION

It is an object of the present invention to provide a ceiling-mounted decontamination unit that includes a housing designed to install, mount, or rest directly on an inverted T-Bar or drop ceiling grid, independent of any other device, incorporating one or more decontamination sources located within the decontamination system's internal space to destroy pathogens, one or more fans inside the system housing that recirculate the air in a room and subject the air to the decontamination source inside the decontamination system housing, destroying bacteria and pathogens in the air passing though the unit's internal space. Room air is drawn into the ceiling-mounted decontamination unit's internal decontamination intake aperture where the contaminated air travels through the systems decontamination chamber, or duct, where the air comes in direct contact with the systems decontamination source that destroys all pathogens in the air. The air decontamination source preferably uses wavelengths ranging from 100 nm to 400 nm. The decontaminated air then passes through the system's exhaust aperture where the air is returned directly, without additional ductwork, from the unit back to the same room.

Unit Directly Connected and Secured to Grid Ceiling.

The ceiling-mounted decontamination unit includes integral provisions, such as pry-out clips, referred to as "Earthquake Clips", designed to secure the ceiling-mounted decontamination unit housing directly to the recessed ceiling grid or T-bar system. These built-in clips are designed to prevent the unit from disengaging from the ceiling grid in the event of an earthquake or other occurrence that may cause a non-supported unit to fall from the ceiling grid toward the floor below. In addition to the integral Earthquake Clips, the unit housing has provisions secure the ceiling-mounted decontamination unit housing to the facility structure by way of support cables or ties, often required by building codes, directly attached to the facility structure. The ceiling-mounted decontamination unit is designed to preferably be permanently attached to the ceiling Grid or T-bar and not move in any way once properly installed.

Unit Connected to Grid Ceiling—not Moveable.

The Recessed Ceiling or Surface Decontamination System housing size, length and width, is greater than the opening size or aperture in a drop ceiling. Once installed, the Recessed Ceiling or Surface Decontamination System housing is designed to remain in complete and direct contact with the ceiling grid at all times. The unit housing is not designed or physically capable of pivoting, hinging, or disengaging in any way from the ceiling grid, downwardly toward room floor for any reason.

Maintenance from Room Side of Installed Unit—not Hinging or Pivoting.

Once installed, all maintenance and access to components within the Recessed Ceiling or Surface Mounted Luminaire are performed from the room side of the installed unit, below the installed unit, with the unit housing remaining in direct contact with the ceiling grid system. All maintenance to the system is performed as installed the unit housing remains in mounted position, on recessed grid ceiling, with access to all components without hinging, pivoting or in any way disengaging the ceiling-mounted decontamination unit housing from the mounted position on the ceiling grid.

Modular—Tool-Free Maintenance.

Costs associated with maintenance and repairs to certain facilities can be costly. Hospitals, offices, and other areas cannot afford to close rooms such as operating rooms, emergency rooms, of high traffic areas for extended periods to make costly repairs on devices in room ceilings. The ceiling-mounted decontamination unit components are modularly designed for quick and tool-free maintenance by way of cord and plug attachment within the unit. Attachable hinge and latch features makes maintenance, service, and replacing components quick, easy, and tool-free. This user-friendly and tool-free design significantly reduces time required to shut down or close a specific room or area during maintenance and repairs.

Center Section—Drop Ceiling Tile (Hinged/Pivot).

The Ceiling or Surface Mounted Decontamination System includes a provision for recessed drop ceiling tile to install into a hingable, frame-like device that allows the drop ceiling tile to attach directly to Ceiling or Surface Mounted Decontamination System to maintain uniformity of the room ceiling appearance. The hingable ceiling tile and frame has the ability to open, by way of device's hinge and latch provisions, in a way that allows the drop ceiling tile to hinge, pivot, or otherwise open downward toward the room floor to access the Ceiling or Surface Mounted Decontamination System's maintenance panel, located or positioned behind the installed ceiling tile, for maintenance to the air decontamination source. The ceiling tile with hingable frame is equipped with a hinge and latch that are compatible with the hinge and latch provision located on the Recessed Ceiling or Surface Mounted System housing. This system includes any and all designs capable of installing into the hinging and latching system as well as other means of attachment including pivot, lift-and-slide, or other known designs as well other securing means such as screws, bolts, clips, spring clips, fasteners, latches, or other known devices known in the art.

Self Contained Air Decontamination System.

The ceiling-mounted decontamination unit is a completely self-contained air decontamination unit, preferably with an anti-microbial finish, that requires no additional devices other than a power supply (currently AC). This system uses internal fans or other mechanisms known in the art to draw room air into one end of the air decontamination system where the air is in direct contact with the decontamination source then the decontaminated, pathogen-free, air is expelled or exhausted from the unit, directly without the need for additional ducts or ductwork. As the air passes through the unit's internal space, the air flows by one or more decontamination sources, preferably Ultraviolet-C, which destroys micro-organisms and pathogens that come into contact with the decontamination source, properly and effectively decontaminating the air before the air exits the unit.

Internal Air Decontamination Sources.

The ceiling-mounted decontamination unit's internal decontamination source and optional external room surface of the present invention is Germicidal Ultraviolet-C (UV-C), preferably ranging from 100 nm to 400 nm wavelength. Ultraviolet light ranging from 100 nm to 400 nm is considered invisible light. Ultraviolet light sources considered less harmful to humans ranging above 400 nm, such as Ultraviolet-B (UV-B), Blacklight, or other visible light spectrum capable of destroying viruses, bacteria, and pathogens are options for both internal air and external surface decontamination systems.

Center Section—Room Light Fixture, Luminaire (Hinged/Pivot).

The Recessed Ceiling or Surface Mounted System's Decontamination System includes a provision for an optional room luminaire. The room luminaire is designed to attach directly to ceiling-mounted decontamination unit, by way of housings hinge and latch provisions, to provide general room lighting. The centrally positioned room luminaire has the ability to open downwardly toward room floor, by way of hinge and latch provisions located on the system housing, that allows access to the system's maintenance panel, located or positioned behind the installed room luminaire, for maintenance to the air decontamination chamber and decontamination source. The custom-size room luminaire is equipped with a hinge and latch that are compatible with the hinge and latch provision located on the Recessed Ceiling or Surface Mounted System housing. This system includes any and all luminaire designs capable of installing into the hinging and latching system as well as other means of attachment including pivot, lift-and-slide, or other known designs as well other securing means such as screws, bolts, clips, spring clips, fasteners, latches, or other known devices known in the art.

Center Section—Room Surface and Air Decontamination Luminaire (Hinged/Pivot).

Yet another option for the Ceiling or Surface Decontamination System includes a provision for a recessed-type Room Surface and Air Decontamination Luminaire to attach directly to Ceiling or Surface Decontamination System housing. This provides a room surface decontamination source or germicidal luminaire designed to destroy viruses, bacteria, and pathogens on room surfaces as well as in the air in the room where the unit is installed. The preferred Room Surface and Air Decontamination Luminaire source for decontamination uses wavelengths preferably ranging from 100 nm to 400 nm, ozone, or other known decontamination sources. The Room Surface and Air Decontamination Luminaire has the ability to open, by way of hinge and latch, in a way that allows access to the Ceiling or Surface Mounted Decontamination System's access panel, located or positioned behind the installed room luminaire, for maintenance to the air decontamination source. All known safety requirement provisions and warnings should be included with this option.

Ozone as Decontamination Source.

Another option for the ceiling-mounted decontamination unit decontamination source is Ozone. Ultraviolet energy can be produced at 185 nm which is proven to effectively produce ozone, a natural sanitizer and deodorizer. Ozone is capable of destroying pathogens in the air and on room surfaces and has the ability to travel deeper into area where the standard or conventional ultraviolet light sources, 200 nm to 400 nm wavelength, may not directly reach. Since UV light sources are required to make contact with surfaces for proper pathogen decontamination, Ozone has the ability to reach areas that UV light sources are not reaching. Additionally, Ozone has ability to decontaminate air and surfaces such as under beds, under desks, behind objects, or any other place in a room where air/gas can travel. When ozone is used as decontamination source for room surface and air decontamination luminaire, a UV light shield device is available to block the UV rays but allow the ozone produced to effectively decontaminate the surfaces and air within a room.

Novel Design and Mounting.

This ceiling-mounted decontamination unit includes provisions to insert or attach a ceiling tile or drop a ceiling tile into a frame that hinges or pivots open from the unit housing and to allow access to the Air Decontamination Chamber maintenance access panel, located in unit housing internal space, to replace the decontamination source or perform maintenance.

The device housing contains provisions that allow the housing to be directly installed onto or into a ceiling surface, recessed drop ceiling or plaster ceiling or non-recessed ceiling, without breaching the air decontamination system in any way.

Furthermore, the ceiling-mounted decontamination unit incorporates a provision to insert a drop ceiling tile into a frame that hinges or pivots open and to allow access to the Air Decontamination Chamber maintenance access panel within the housing for maintenance to the decontamination chamber and decontamination source. This provision allow for the hingable ceiling tile in frame, hingable room luminaire, or hingable recessed surface and air decontamination luminaire to be interchangeable at any time without the need for any modifications to the system.

The room luminaire provision feature includes a hinge and latch provision, once the room luminaire is installed onto the hinge system, allows the room luminaire to hinge or pivot downwardly, toward the room floor, from the mounted position in the drop ceiling to allow access to the ceiling-mounted decontamination unit maintenance panel located within the housing's internal space.

The features of the Recessed Ceiling or Surface Decontamination allow for interchangeability as well as tool-free removal and replacing the hingable ceiling tile, room luminaire, and room air and surface decontamination luminaire.

Unique Luminaire Power Supply Connection in System.

The optional feature such as the Room Luminaire and Room Surface and Air Decontamination Luminaire are designed to connect directly into the ceiling-mounted decontamination unit internal power supply connection. These dedicated connectors are uniquely specific to each hingable, attachable and removable device provision and designed to provide power to each device. The power supply connection from the ceiling-mounted decontamination units consists of a power supply provision for room luminaire and room surface decontamination luminaire consist of a modular connection system, preferably female-type but other system is acceptable. Although the dedicated connectors are similar in function to an electrical wall outlet and designed to only accept similar male connector supplied on the optional Room Luminaire or Room Surface and Air Decontamination Luminaire. In the preferred embodiment of this system, the power supply connecting system is incorporated into all ceiling-mounted decontamination unit and available if needed or not. Units incorporating Drop Ceiling Tile in hingable frame will not require power supply provision but in the preferred embodiment the provision will be included in case a customer wishes to replace a drop ceiling tile with a room luminaire or a room surface decontamination luminaire at a later date.

Optional Center Luminaire Hinge and Latch System.

The attached Room Luminaire, Recessed Ceiling Tile in frame, or Room Surface and Air Decontamination Luminaire include a hinge and latch provision which function in either direction that allows to unit to disconnect from the ceiling-mounted decontamination unit housing for quick and easy maintenance or replacement if needed.

Optional Center Luminaire Removable/Detachable Feature.

The ceiling-mounted decontamination unit combines an internal air chamber and a decontamination source with a removable and detachable room luminaire feature that pivots or hinges from the provisions attached to the Recessed Ceiling or Surface Mounted Germicidal Air Decontamination System. The Room Luminaire and Room Surface and Air Decontamination Luminaire systems contain attachment cords with modular connections making the units easy to unplug and disconnect from power supply to allow for easy tool-free luminaire replacement.

Tool-Free Center Luminaire and Room Surface Luminaire Replacement.

The ceiling-mounted decontamination unit's hingable Room Luminaire and Room Surface and Air Decontamination Luminaires are modularly designed with all necessary components attached to the Luminaire housing. To remove or replace, simply disconnect the power supply connector by releasing connector locking provision and unhook/release the hinge/pivot provision to remove the luminaire from the ceiling-mounted decontamination unit housing. To install a new or replacement luminaire, reverse the previous steps.

Installs in Same Space as Traditional Luminaire.

One preferred embodiment for the ceiling-mounted decontamination unit includes provisions, between the air intake and air exhaust apertures, for a room luminaire. Due to limited space in facilities, the addition of an air decontamination device may not be possible. Most rooms are designed with lighting fixtures centrally located in the ceilings with power supply to the unit. Incorporating a room luminaire into a Recessed Ceiling or Surface-type Germicidal Air Decontamination system allows for a combination unit to function in the same physical space as the existing recessed room luminaire providing the additional feature of air decontamination in optimal locations.

Decontaminated Air Returned Directly to Room—No Ductwork Needed.

This device re-circulates the decontaminated air from the unit's decontamination chamber directly back into the same room without the need for additional ductwork or other devices. By directly re-circulating pathogen-free air from the internal decontamination chamber and directly back into the same room, this device is suitable for all room types with all ceiling types. Since this device does not require additional ductwork to re-circulate the decontaminated air back into the room, this device is also suitable for sheetrock/plaster ceilings, concrete ceilings, and other non-recessed type ceilings. When installed in recessed ceilings, this device does not interfere with various obstacles above a ceiling such as HVAC ductwork, telecom, electrical wiring and conduit, water lines, water sprinkler systems, as well as other infrastructure items and structures.

Optional Air Filters.

The ceiling-mounted decontamination unit may contain air filter systems located at the air intake aperture or air exhaust aperture, positioned prior to or after the decontamination chamber where the air is decontaminated, which may be accessible for maintenance by way of vent cover, grill, or access panel that is removable, hinged, or using other methods that do not require the unit to be moved, removed, pivoted, hinged, altered, or removed or relocated in any way from its installed/mounted operating position. The air filter is designed to be located at or on the vertical intake or exhaust ducts and not in the actual decontamination chamber in a way that the filter does not interfere with the decontamination chamber where the air flow makes contact with the decontamination source. This also protects the air filter from the UV rays when UV is the decontamination source.

Air Decontamination Source Access Panel.

The Recessed Ceiling or Surface Decontamination System has an air decontamination source maintenance cover to access the air decontamination chamber or duct for replacement or maintenance to the system air decontamination source. The Room Luminaire, Drop Ceiling Tile in hinged frame, and Room Surface and Air Decontamination Luminaire are all designed to pivot or hinge open 90 degrees, in a downward direction toward the floor, for access to the systems maintenance panel to allow access to the decontamination source for maintenance or replacement. The air decontamination maintenance panel does not require the Recessed Ceiling or Surface Decontamination System unit to be moved, removed, pivoted, hinged, altered, or removed or relocated in any way from installed mounted operating position for unit maintenance or replacing the decontamination source.

Room Luminaire—Dimming Capable.

The Recessed Ceiling or Surface Decontamination System center Room Luminaire is preferably capable of dimming.

Indicator Light.

The Recessed Ceiling and Surface Decontamination System preferably contains an indicator light to confirm when the internal air decontamination system is or is not working properly or requires maintenance.

Air Decontamination Source Power-Off Switch.

The Recessed Ceiling or Surface Decontamination System preferably has a switch to shut down power to the internal decontamination chamber when the air decontamination access cover is opened or removed for access or maintenance. The switch may be manual, but it is preferably automatic, activating when the Room Luminaire, Drop Ceiling Tile in hinged frame, or Room Surface and Air Decontamination Luminaire are opened.

External Room Surface Decontamination Source.

The Recessed Ceiling or Surface Decontamination System preferably includes a warning strobe light, flashing light, audible alarm, and/or another warning device, or combination of warning devices, when the unit switches from external visible light source to the optional external non-visible light source (UV) for room decontamination.

Occupancy Sensor.

The Recessed Ceiling or Surface Decontamination System optional External Room Surface and Air Decontamination Luminaire will contain occupancy sensors, thermal sensor, or motion sensor devices to control lighting when the room is occupied versus unoccupied. The sensor may be passive infrared, ultrasonic, dual passive infrared and Ultrasonic or other type of sensors known in the art.

Visual Warning Feature.

The Recessed Ceiling or Surface Decontamination System optional External Room Surface and Air Decontamination Luminaire will contain visual warning feature such a strobe, strobe light, or other means as an indicator that the Room Surface and Air Decontamination Luminaire is in use.

Online Monitoring.

The Recessed Ceiling or Surface Decontamination System preferably includes an online or other type monitoring system, on site or remote, which alerts installation facility or others that system that is working properly or is not working properly and requires maintenance.

BRIEF DESCRIPTION OF THE DRAWINGS

A system and device for decontaminating air from a ceiling device in offices, hospitals, health care, commercial businesses, or similar facilities will now be described by way of example with reference to the accompanying drawings in which.

Figure 1:
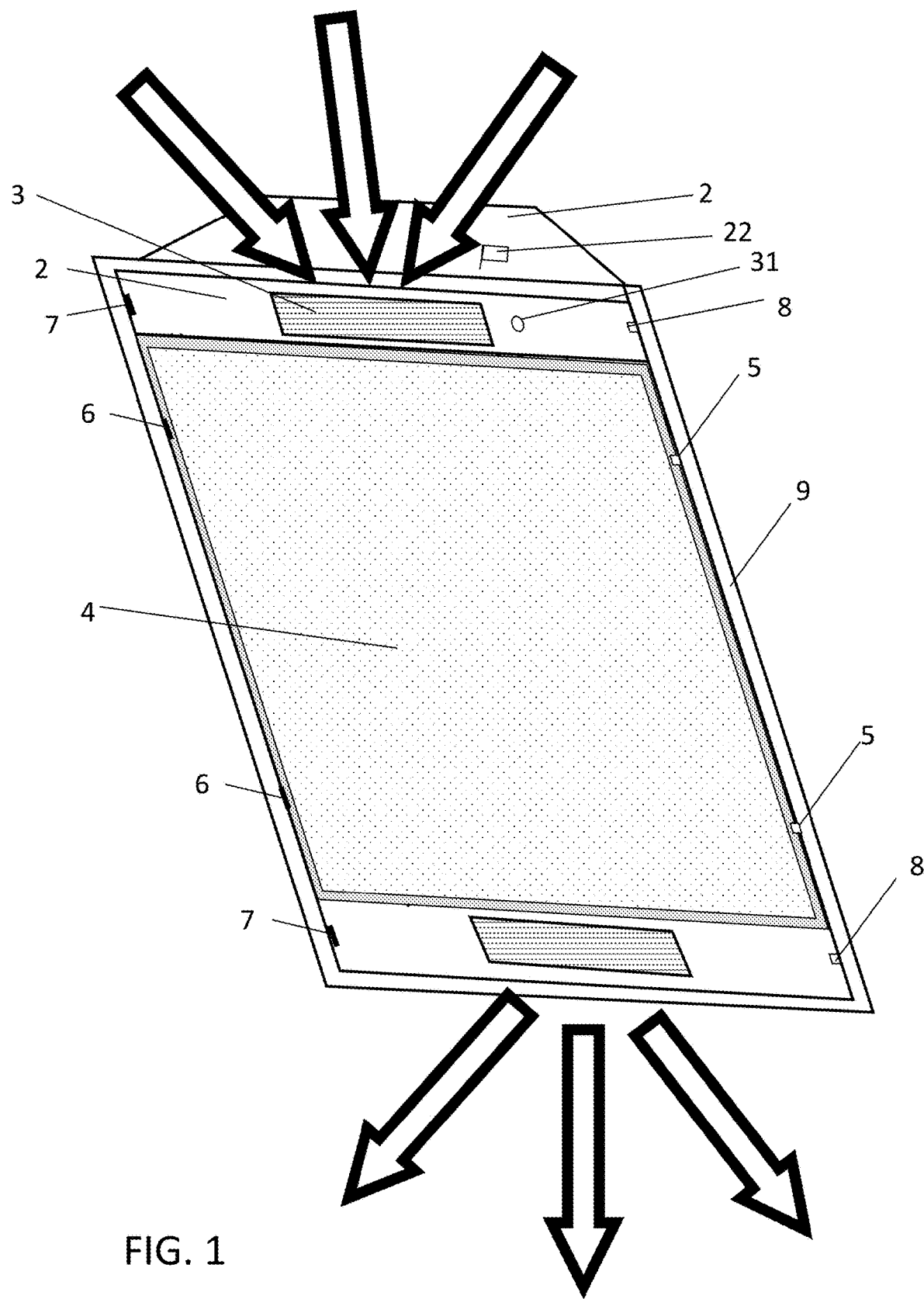
FIG. 1 is a front perspective view of the Ceiling-Mounted Decontamination Unit with of the present invention with hingable ceiling tile installed.
Figure 2:
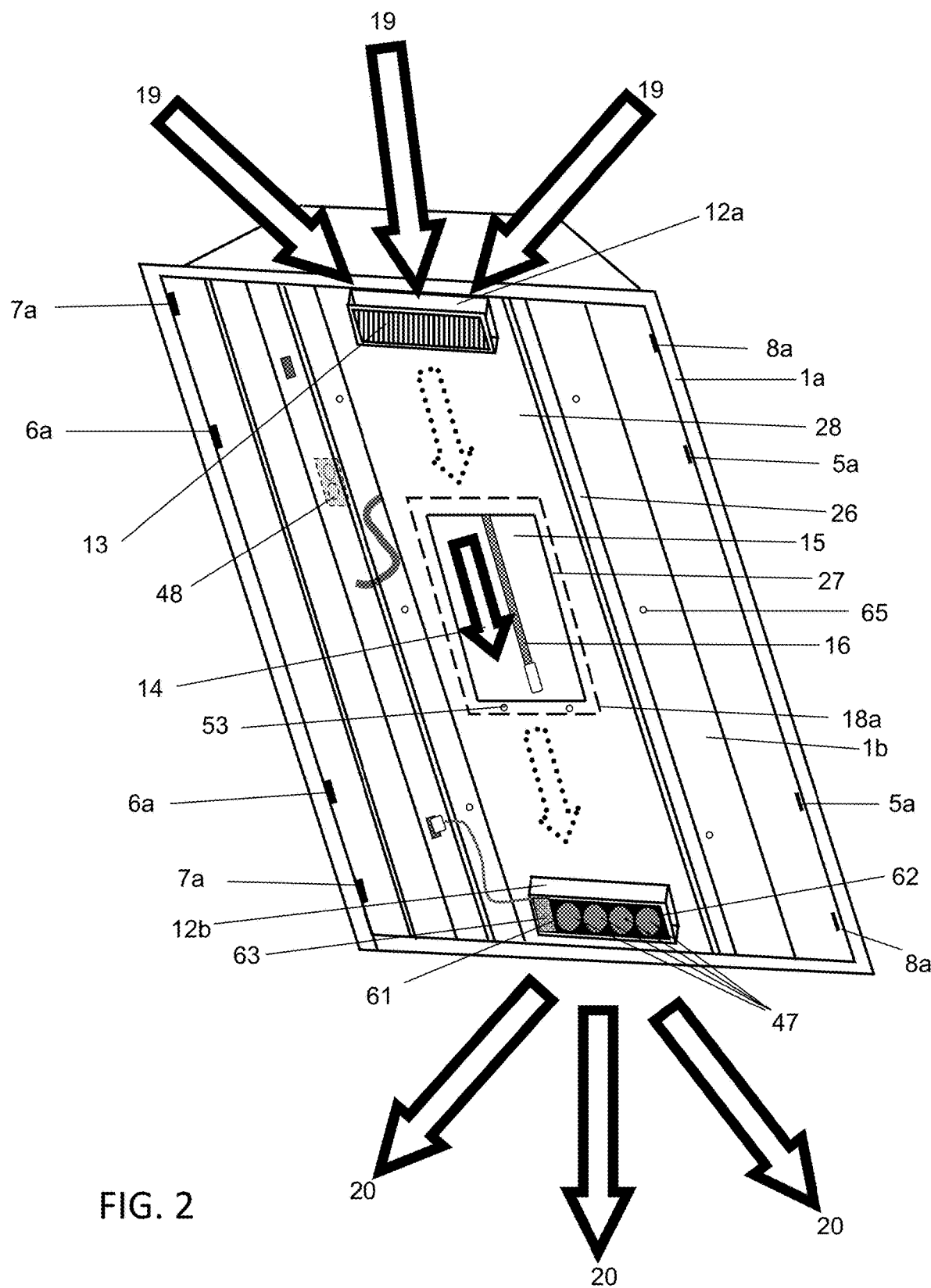
FIG. 2 is a front perspective view of the air flow path for the Ceiling-Mounted Decontamination Unit of present invention illustrated in FIG. 1.
Figure 3:
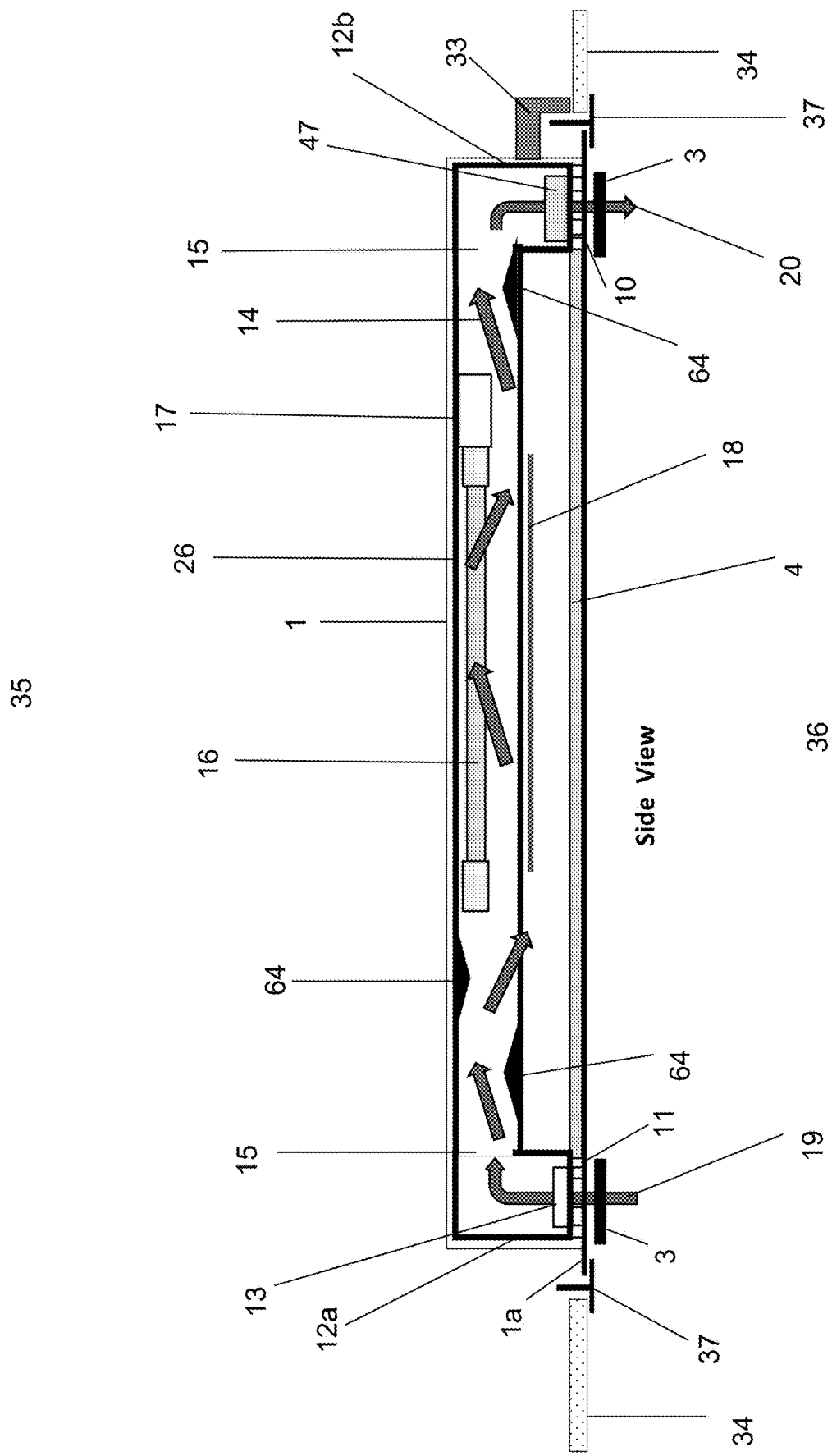
FIG. 3 is a side view cross section of the Ceiling-Mounted Decontamination Unit of present invention with of FIG. 1 of showing air path and identified components.
Figure 4:
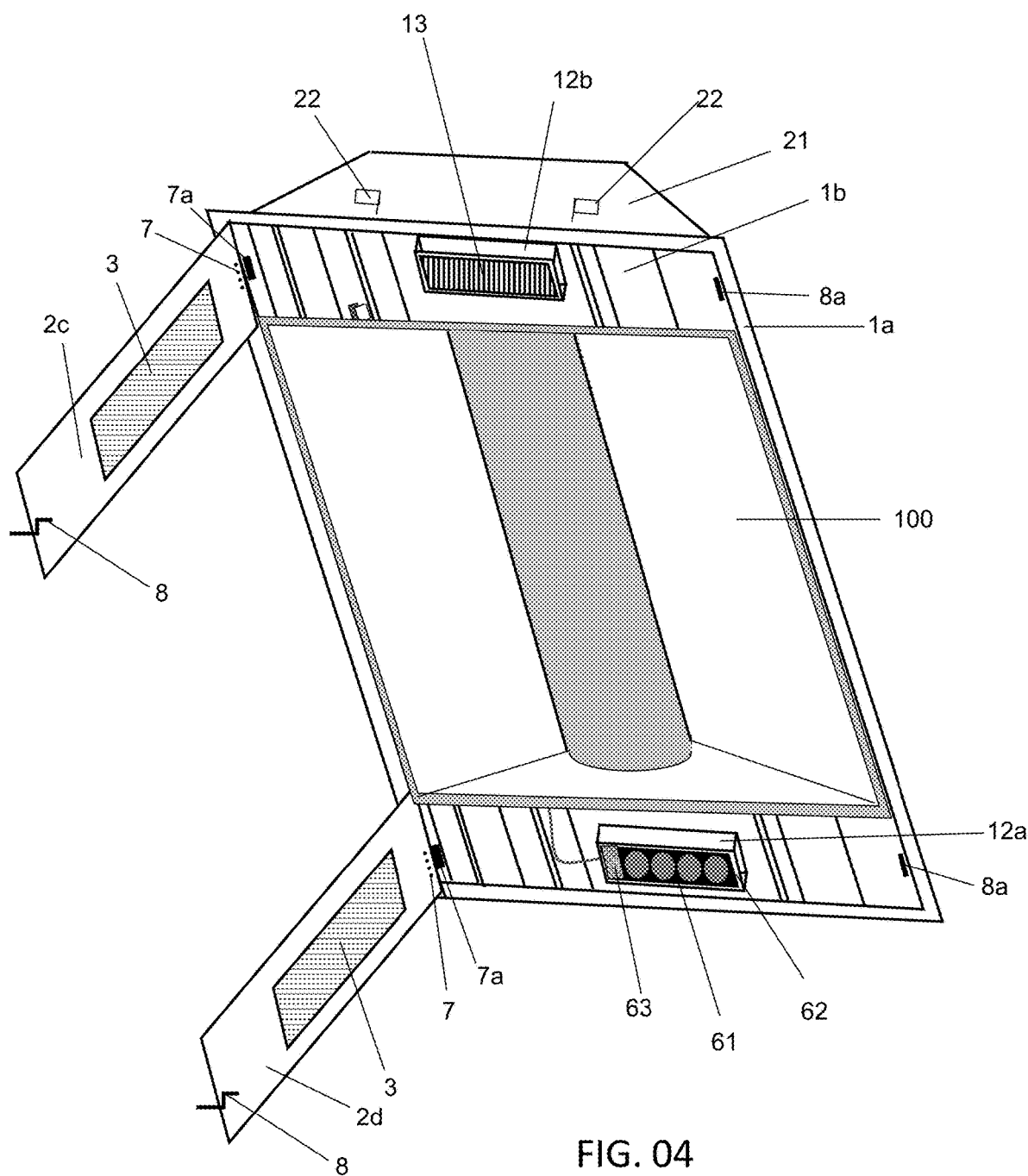
FIG. 4 is a perspective view of the Ceiling-Mounted Decontamination Unit of present invention showing alternate embodiment of FIG. 1 with Optional Room Luminaire in closed position, hingable intake aperture and hingable exhaust aperture are in open position, and identified components.

The following is a table of elements with numeral references illustrated in the drawings:

| Part No.: | Description |
|---|---|
| 1 | Housing/Body |
| 1a | Housing Flange Rest on T-Bar/Grid Ceiling |
| 1b | Housing Internal Space |
| 2a | Intake Aperture - Closed Position |
| 2b | Exhaust Aperture - Closed Position |
| 2c | Intake Aperture - Open Position |
| 2d | Exhaust Aperture - Open Position |
| 3 | Vent Grille Cover |
| 4 | Ceiling Tile Hinge |
| 5 | Center Latch (on Ceiling Time - Luminaire) |
| 5a | Center Latch Provision oh Housing |
| 6 | Center Hinge (on Ceiling Tile - Luminaire) |
| 6a | Center Hinge Provision on Housing |
| 7 | End Hinge (Intake/on Exhaust Aperture) |
| 7a | End Hinge Provision on Housing |
| 8 | End Latch (on Intake/Exhaust Aperture) |
| 8a | End Latch Provision on Housing |
| 9 | Ceiling Tile/Lens in Frame |
| 10 | Air Exhaust Aperture |
| 11 | Air Intake Aperture |
| 12a | Vertical Duct (Intake) |
| 12b | Vertical Duct (Exhaust) |
| 13 | Filter |
| 14 | Air Moving Through Decontamination Chamber |
| 15 | Air Decontamination Chamber (Interior) |
| 16 | Internal Air Decontamination Source |
| 17 | Connection for Decontamination Source |
| 18 | Maintenance Panel for Decontamination Chamber |
| 18a | Maintenance Panel for Decontamination Chamber (Closed Position) |
| 19 | Air Entering Intake Aperture |
| 20 | Air Exiting Exhaust Aperture |
| 21 | Housing End |
| 22 | Integral Hurricane Clip |
| 23 | Intake/Exhaust Vertical Duct |
| 24 | Provision in Intake or Exhaust Aperture for Indicator Light |
| 25 | Provision in Intake or Exhaust Aperture for Occupancy Sensor |
| 26 | Air Decontamination Duct/Chamber Base |
| 27 | Opening in Chamber for Maintenance |
| 28 | Air Decontamination Duct/Chamber Cover |
| 29a | Power Supply Connection for Means for Driving Air (Female) |
| 29b | Power Supply Connector from Luminaires (Female) |
| 30 | Cable from Air Decontamination Source to Power Supply |
| 31 | System Failure Indicator Light for Air Decontamination Chamber |
| 32 | Detachable Hinges for LED Mounting Surface (43) |
| 32A | Hinge Provision for LED Array |
| 33 | Hurricane Clips on Ceiling Grid |
| 34 | Drop Ceiling Tile in T-Bar/Grid Ceiling |
| 34b | Plaster Ceiling |
| 35 | Area Above Recessed Ceiling |
| 36 | Area Below Recessed Ceiling |
| 37 | Recessed Ceiling T-Bar/Grid |
| 38 | Electrical Raceway Cover |
| 39 | Components in Raceway |
| 40 | Electrical Raceway |
| 41 | Ceiling Tile In frame in closed position connect to Housing |
| 42 | Ceiling Tile In Frame In Open Position (Hinged 90 Degrees) |
| 43 | LED Array/Module Mounting Surface |
| 43a | LED Array/Module Mounting Surface (Open Position) |
| 43b | ED Array/Module Mounting Surface (Closed Position) |
| 44 | Room Luminaire Electrical Raceway with Connecting Cord |
| 45 | Full Size Flat Panel Luminaire Electrical Enclosure |
| 46 | LED (Source) Array/Module for Room Lighting |
| 46a | LED (Source) Array/Module for Room Lighting (Open Position) |
| 46b | LED (Source) Array/Module for Room Lighting (Closed Position) |
| 46c | Driver or Power Supply for LED Array (46) |
| 47 | Means for Driving Air |
| 48 | Access Plate connected to Unit Housing |
| 49 | Power Supply for Full Size LED Flat Panel Unit (Unit Closed) |

-continued

| Part No.: | Description |
| --- | --- |
| 50 | Power Supply for Full Size LED Flat Panel (Unit Open) |
| 51 | Internal Decontamination Chamber (Open Position) |
| 52 | Means for Securing LED Mounting Surface (43) |
| 52a | Provision for securing LED Mounting Surface 52 to Housing |
| 53 | Maintenance Panel Provision for Mounting |
| 54 | Maintenance Panel Means for Attachment to Chamber |
| 55 | Tabs or Provision to Secure Housing/Unit to Building Structure |
| 56 | Connector from Means for Moving Air(fans) to Power Supply (male) |
| 57 | Power Cord from Means for Moving Air (fans) to Power Supply |
| 58 | Connector from Room Luminaire to Power Supply (male) |
| 59 | Power Cord from Room Luminaire to Power Supply |
| 60 | Occupancy Sensor |
| 61 | Fan Bank |
| 62 | Fan Bracket |
| 63 | Fan Power Supply |
| 64 | Air Deflector |
| 65 | Holes (Knockouts) for Surface Mounting |
| 66 | Door Switch |
| 67 | Surface Mount Decorative Trim |
| 68 | Hardware securing unit to non-recessed ceiling surface |
| 100 | Room Luminaire (Hinged) "V" Type |
| 100a | Room Luminaire (Hinged) "V" Type (Open Position) |
| 100b | Room Luminaire (Hinged) "V" Type - Closed Position |
| 100c | Single Piece Room Luminaire with Vents included |
| 101 | Room Luminaire (Hinged) Flat Panel |
| 101a | Room Luminaire (Hinged) Flat Panel (Open Position) |
| 101b | Room Luminaire (Hinged) Flat Panel - Closed Position |
| 102 | Full Size Flat Panel with Apertures and Vents |
| 102a | Full Size Flat Panel with Apertures and Vents (Open Position) |
| 102b | Full Size Flat Panel with Apertures and Vents (Closed Position) |
| 103 | Lens (Prismatic, White, or Other) |
| 103a | Lens Prismatic, White, or Other (Open Position) |
| 103b | Lens Prismatic, White, or Other (Closed Position) |
| 104 | External Surface and Air Decontamination Luminaire |
| 104a | External Surface and Air Decontamination Luminaire (Open Position) |
| 104b | External Surface and Air Decontamination Luminaire (Closed Position) |
| 105 | External Surface and Air Decontamination Source |
| 106 | External Surface and Air Decontamination Source UV Shield for Ozone System |
| 107 | UV Shield attachment Clip to attach to Decontamination Source |
| 108 | Internal Air Decontamination Source Single Panel (Open Position) |
| 109 | Internal Air Decontamination Source Single Panel (Closed Position) |
| 110 | Ductless Air Decontamination Chamber |

DESCRIPTION OF THE PREFERRED EMBODIMENT

It is an object of the present invention to provide a ceiling-mounted decontamination unit with an internal decontamination source, with air intake and exhaust, which creates air movement through the unit's internal air decontamination chamber, duct, or enclosure to decontaminate and circulate room air effectively when the unit is installed into or onto a ceiling. This ceiling-mounted decontamination unit draws air into system from room below, decontaminates the air inside the chamber (enclosure), and exhausts air directly into the room below (drawing air upward into the air intake and exhausting the air downward into the room directly from the unit).

Permanently (Non-Moveably) Installed into Recessed Ceiling.

The ceiling-mounted decontamination unit is designed to be installed in a fixed, permanent, non-moveable manner into or onto recessed ceilings, drop ceiling, Inverted T-Bar Ceiling, Grid Ceiling, or other known type of suspended ceilings as well as onto or into non-recessed or plaster or sheetrock ceiling in areas such offices, hospitals, hallways, health care facilities, and other locations where air decontamination is desired.

Provision for Room Ceiling Tile, Luminaire, or Room Surface Decontamination Luminaire.

The ceiling-mounted decontamination unit contains a provision, preferably between the intake aperture and exhaust aperture or vent grill covers, designed to couple a Ceiling Tile in frame when no luminaire is needed, Room Luminaire for room lighting, or a Room Surface and Air Decontamination Luminaire for decontaminating room surfaces and air in the room or area where the unit is installed.

Ceiling Tile, Luminaire, Room Decontamination are Hingable or Pivoting.

The Ceiling Tile, Room Luminaire, and Room Surface and Air Decontamination Luminaire coupled to the ceiling-mounted decontamination unit provision, are designed to hinge or pivot directly from the ceiling-mounted decontamination unit housing in a downward direction, toward the room floor, for maintenance, removal, and replacement, as well as provide access to the electrical raceway and Air Decontamination Maintenance Panel located on the decontamination chamber in the housing's internal space located behind the installed Ceiling Tile, Room Luminaire, and Room Surface and Air Decontamination Luminaire. This allows for all maintenance, replacement, removal, or any service from below the installed unit without moving or disengaging the unit housing from the ceiling grid in any way.

Internal Decontamination Source.

The ceiling-mounted decontamination unit contains an internal decontamination system that is designed to draw room air into the system's internal decontamination chamber, where a decontamination source (Ultraviolet-C, Germicidal, Light Emitting Diode (LED), fluorescent, Ozone, or any other decontamination source) kills airborne pathogens in the room air as the air travels through the system's internal decontamination chamber making direct contact with the internal decontamination source. In the preferred embodiment, the one or more decontamination source(s) located within the decontamination chamber is positioned parallel with the air flowing through the chamber to increase the exposure time required for effective decontamination. Orienting the decontamination source parallel with the air flow increases the exposure time between the air in the chamber and the decontamination source. Greater exposure allows for more effective pathogen decontamination. Positioning the decontamination source in a parallel orientation with the air flow significantly increases the effectiveness of the germicidal source and the decontamination process verses orienting the decontamination source oriented in a position perpendicular with the air flow path through the decontamination chamber. The air makes direct and continued contact with the germicidal source as the air travels through the chamber. The decontaminated air exits the decontamination chamber and exits the unit directly back into the same room.

Room Surface and Air Decontamination Source.

The ceiling-mounted decontamination unit may also contain a Room Surface and Air Decontamination Luminaire consisting of germicidal ultraviolet light (UV-C), Germicidal, Ozone, Sonic, Ultrasonic or known decontamination source designed to destroy pathogens on surfaces or in air as they come into contact with the Room Surface Decontamination Luminaire source. The Room Surface Decontamination Luminaire may consist of Light Emitting Diode (LED), fluorescent, germicidal, ultraviolet (UV-C), Ozone, or any other known decontamination source.

Source of Invisible Light Less than 400 Nm.

Both the internal Air Decontamination source and Room Surface and Air Decontamination Luminaire source are preferably "invisible light" less than 400 nm in wavelength. The lighting may be LED, fluorescent, germicidal, ultraviolet (UVC), ozone or other decontamination-type source or other lighting known in the art.

UV-C, Germicidal, LED, Sonic, Ultrasonic, Ozone as Decontaminating Sources.

Currently, UV-C (Ultraviolet-C) in fluorescent-type discharge linear tubes with bi-pin or quad-pin base is the most effective decontamination system on the market with wavelengths of approximately 254 nm (254 nanometers). The preferred wavelength for the application is 254 nm-270 nm, which is believed to be the wavelength for maximum pathogen destruction. LED technology allows UV source to produce various wave lengths, producing wavelengths with greater pathogen decontamination ability. UV-C is a pathogen-killing light source that is unsafe for human contact. A decontamination source using UV-C is not visible light, so it would be dangerous to humans, mostly eyes and skin, if not treated safely. However, other methods of destroying bacteria, such as sound or ultrasound technology, and ozone may be used to destroy pathogens. In that case, the decontamination source would not be light (UV spectrum based), but sound based of air/gas-based and implementing the system and device of the present invention would simply involve replacing the UV-C light decontamination source with the sound, ultrasound based decontamination source or an ozone source.

With reference to FIGS. 1-6, the preferred embodiment of the present invention achieves this goal with a housing 1, which includes attached ends 21, being substantially rectangular for installing the unit directly onto a recessed ceiling grid or T-Bar 37, also referred to as suspended ceiling, T-Bar Ceiling, Inverted T-Bar Ceiling, Grid Ceiling, or other known references. The housing 1 is adapted to be placed directly on the Recessed Drop Ceiling Grid "T-Bar" 37 as well as into or onto a plaster ceiling or other Non-Drop Ceiling applications inside a room. The ends 21 includes provisions, build in Hurricane Clips 22 designed to interlock the housing 1 with the ceiling grid 37 to prevent the housing from moving or dislodging from the grid ceiling 37 after installation. The ends 21 also include pry-out provision tabs 55 designed to fold or bend away from the end 21, toward the ceiling, and provide additional provisions for support cable or support wire that secure the housing 1 directly to the facility structure to prevent the unit from dislodging or disengaging from the ceiling grid 37 after installation.

The housing 1 interior space 1b provides a mounting surface or raceway and electrical raceway cover 38 in which the internal components 39 of the Recessed or Surface Germicidal Decontamination System are mounted, including an internal air decontamination chamber 15, intake aperture 2a and exhaust aperture 2b, electrical raceway 40, means for driving air 47, and other required devices.

Decontamination Chamber/Duct.

The internal space 1b of housing 1 also contains at least one decontamination duct or chamber 15 consisting of a vertical intake duct 12a, decontamination chamber base 26 and chamber cover 28, and vertical exhaust duct 12b located within the housing 1. The decontamination chamber or duct 15 is positioned to extend the length of the housing 1 for greater exposure time to the decontamination source 16 in the chamber 15. The room air 19 is drawn through the air intake aperture 2a, by the system's means for driving air 47 which are preferably air fans 61, and into the system's internal decontamination chamber 15 where the air 14 in the chamber 15 travels across one or more air deflectors 64 extending perpendicular across the chamber designed to create a stirring and swirling effect that causes an unsteady movement of air in the chamber. The air in the chamber 14 comes in direct contact with the decontamination source 16, oriented in a direction that is perpendicular with the direction of the air path 14 traveling through the decontamination chamber for proper and effective decontamination. The decontaminated air exits the internal decontamination chamber 15 by way of the unit's exhaust aperture 2b where the decontaminated air returns to the same room, directly from the unit 20, without the need for additional fans, ductwork, or HVAC equipment. The system's internal decontamination chamber 15 contains an opening 27 with a removable maintenance panel 18 designed for maintenance to the chamber 15 and the internal decontamination source 16 including replacing the decontamination source 16.

Internal Decontamination Source.

At least one internal decontamination source 16 is placed, attached or mounted into the decontamination chamber 15 positioned parallel with the air 14 flow to increase the exposure time between the decontamination source 16 and air 14 flowing through the chamber 15 for effective decontamination, located inside the internal space 1b of the housing 1. Also contained in the internal space 1b of the housing 1 are the means for driving air 47 through the decontamination chamber 15, wherein the air 14 is decontaminated by the at least one internal decontamination source 16 when the air 14 passes through the decontamination chamber 15. The means for driving air 47 are preferably air fans 61, but they could be other means for driving air. Thus, with reference to FIG. 3, the means for driving air 47 take room air 19 into the internal space 1b of the housing 1, through the intake aperture 2a and drive the air 19 into the decontamination chamber 15. When the at least one internal decontamination source 16 is active, pathogens and bacteria are killed or disabled when air 14 is passing through the decontamination chamber 15.

Means for Driving Air.

The means for driving air 47 then exhaust decontaminated air 20 from the internal space 1b of the housing 1 through the exhaust aperture 2b. The means for driving air 47 may include optional air filters 13, such as, for example particular matter, HEPA, or other known filters. The directional arrows 19 show the path of air 19 flow that enters the chamber 15 through the intake aperture 2a and the directional arrow 20 shows the path of the decontaminated air 20 flow that exits the system exhaust aperture 2b. The directional arrows 14 show the path of the air 14 flow across the air deflectors 64 and the decontamination source 16 located within the decontamination chamber 15. The intake aperture 2a and/or the exhaust aperture 2b of the preferred embodiment include a hinge 7 designed to engage and secure the intake aperture 2a and exhaust aperture 2b to the hinge provision 7a in the housing. The intake aperture 2a and exhaust aperture 2b are secured to the housing by a latch mechanism 8 designed to engage in the latch slot 8a to allow intake aperture 2a and exhaust aperture 2b to hinge or pivot open and/or to detach from housing 1 to enable easy access to the means for driving air 47 as well as air filters 13 for maintenance and/or replacement. The means for driving air 47, preferably fans or fan bank 61, are modular and connected together with fan bracket 62 that includes an enclosure for the fan power supply 63.

Hingable Lighting.

Figure 7:
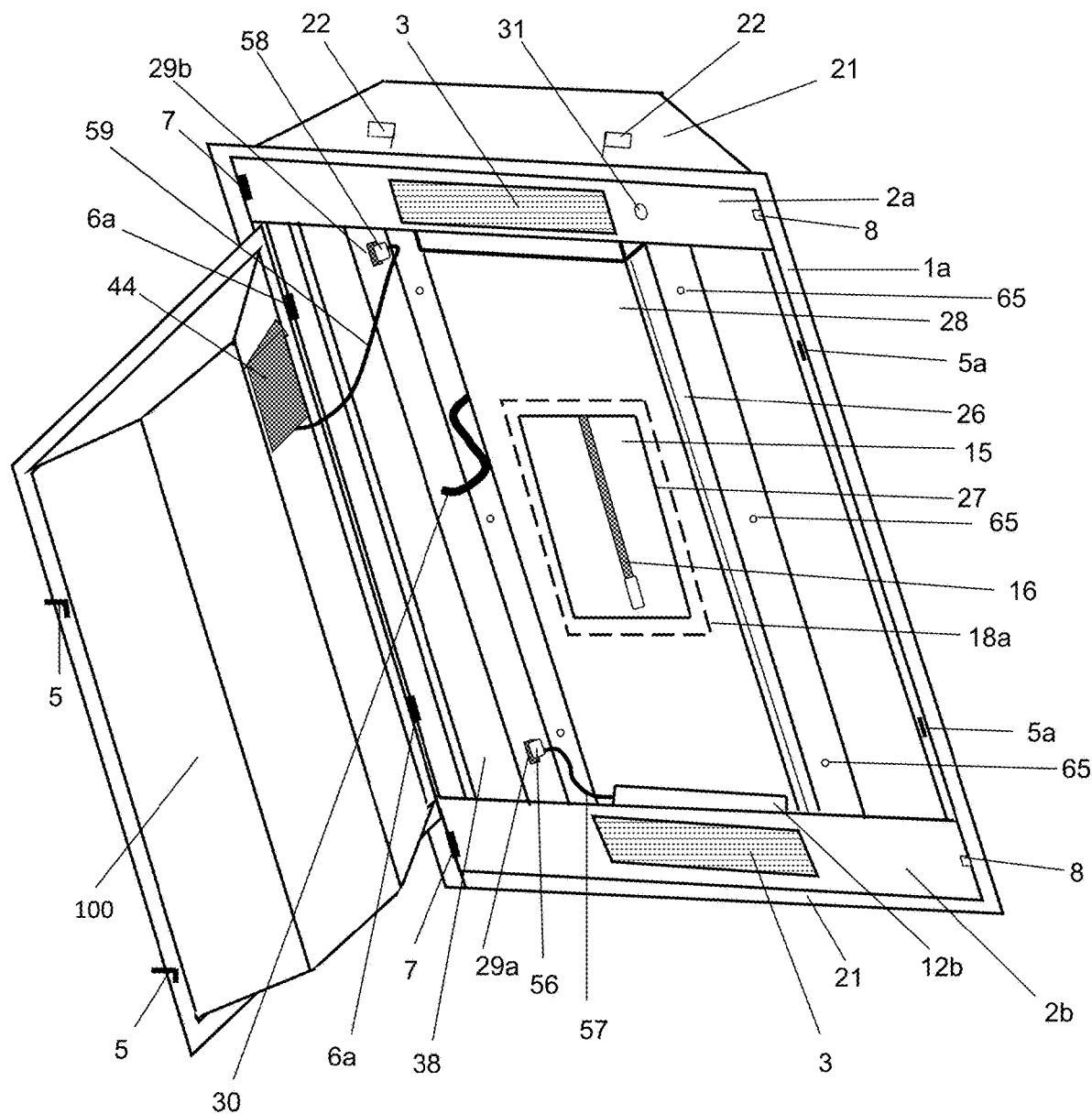
FIG. 7 is a perspective view of the Ceiling-Mounted Decontamination Unit of the present invention showing alternate embodiment of FIG. 1 with installed optional room luminaire in open position and identified components.
Figure 8:
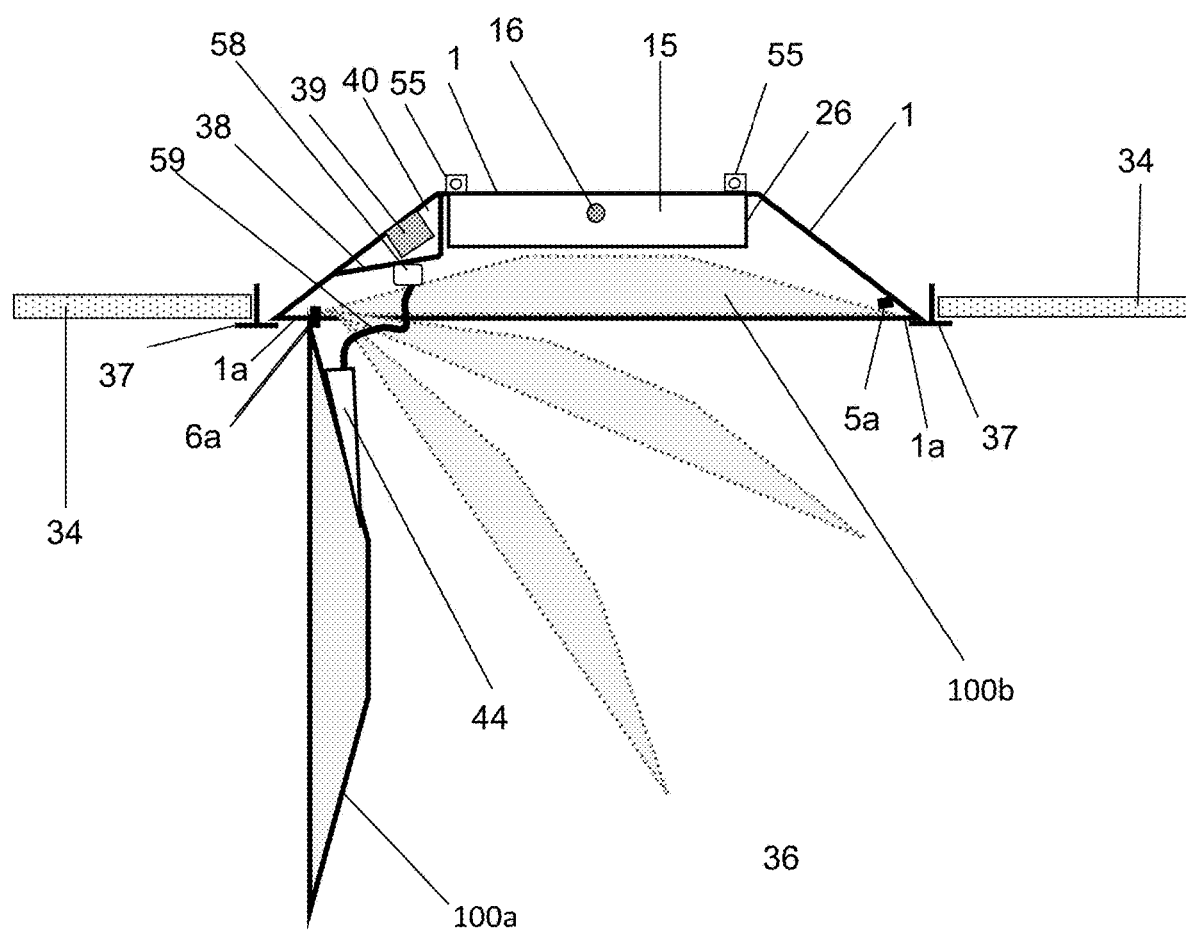
FIG. 8 is an end view of the Ceiling-Mounted Decontamination of present invention showing alternate embodiment of FIG. 1 and identified components.
Figure 9:
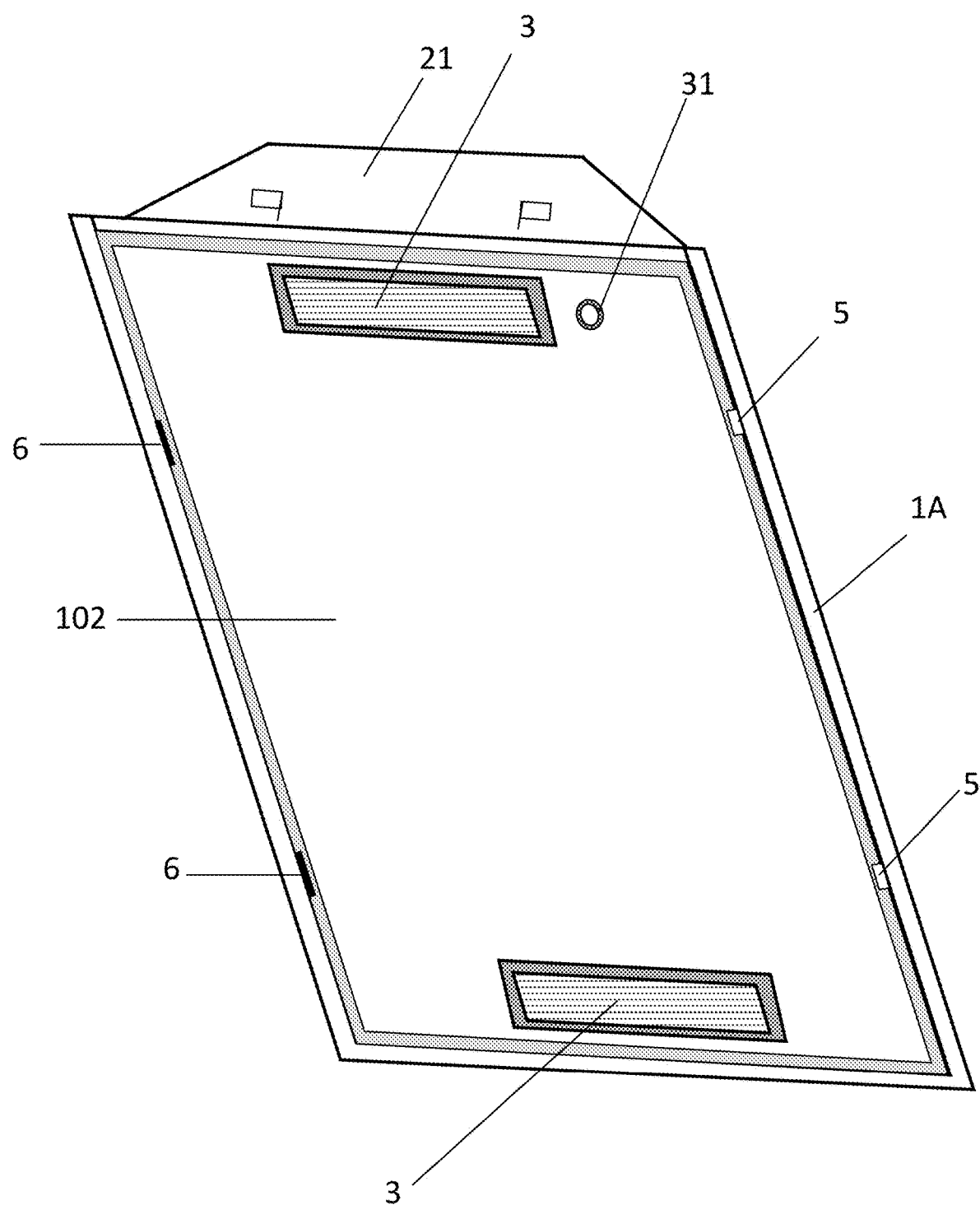
FIG. 9 is a perspective view of the Ceiling-Mounted Decontamination Unit of present invention showing alternate embodiment with installed Optional Full LED Panel Unit installed.
Figure 10:
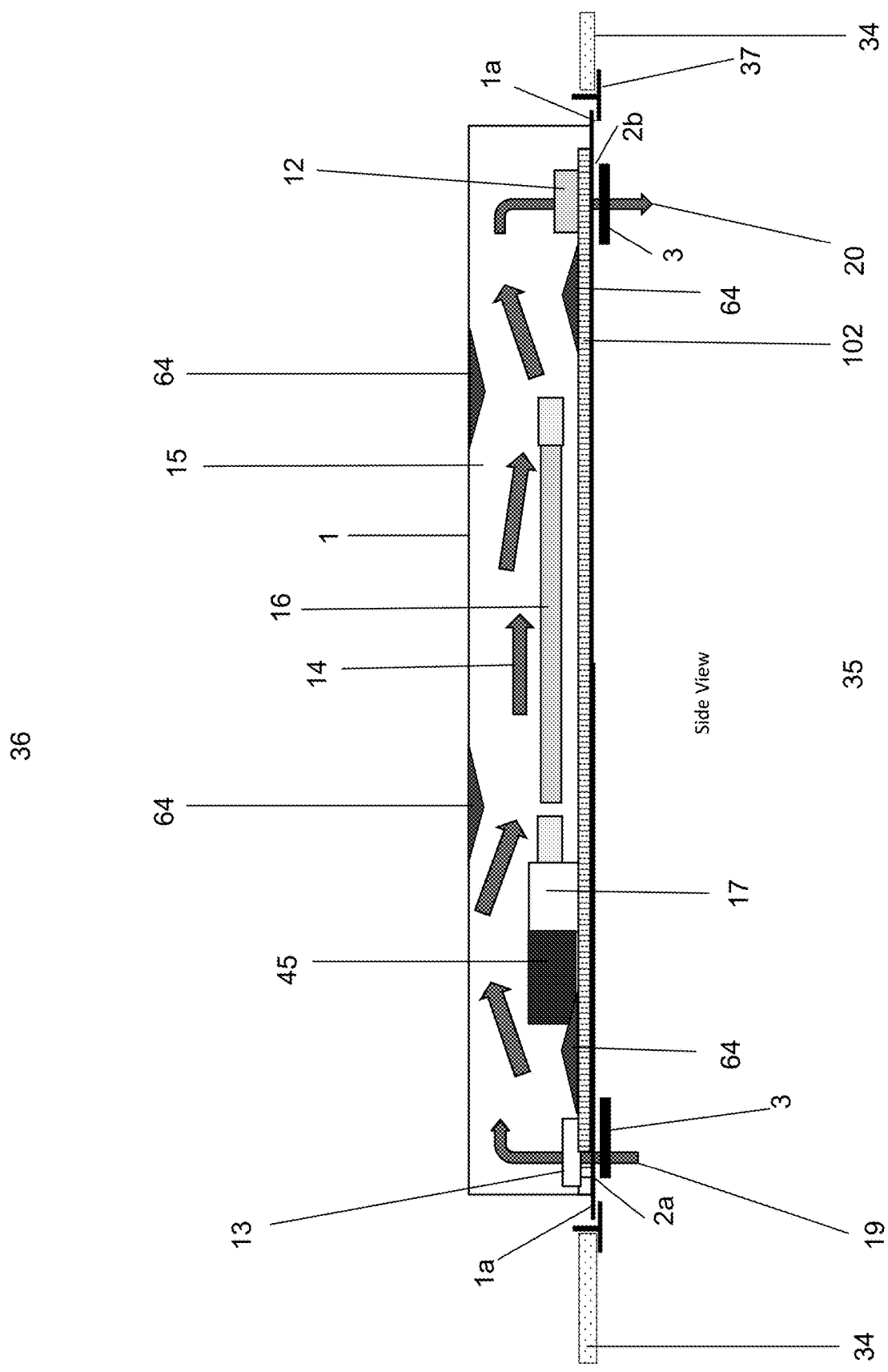
FIG. 10 is a side view cross section of the Ceiling-Mounted Decontamination Unit of present invention with alternate embodiment of FIG. 9 showing air path and identified components.
Figure 11:
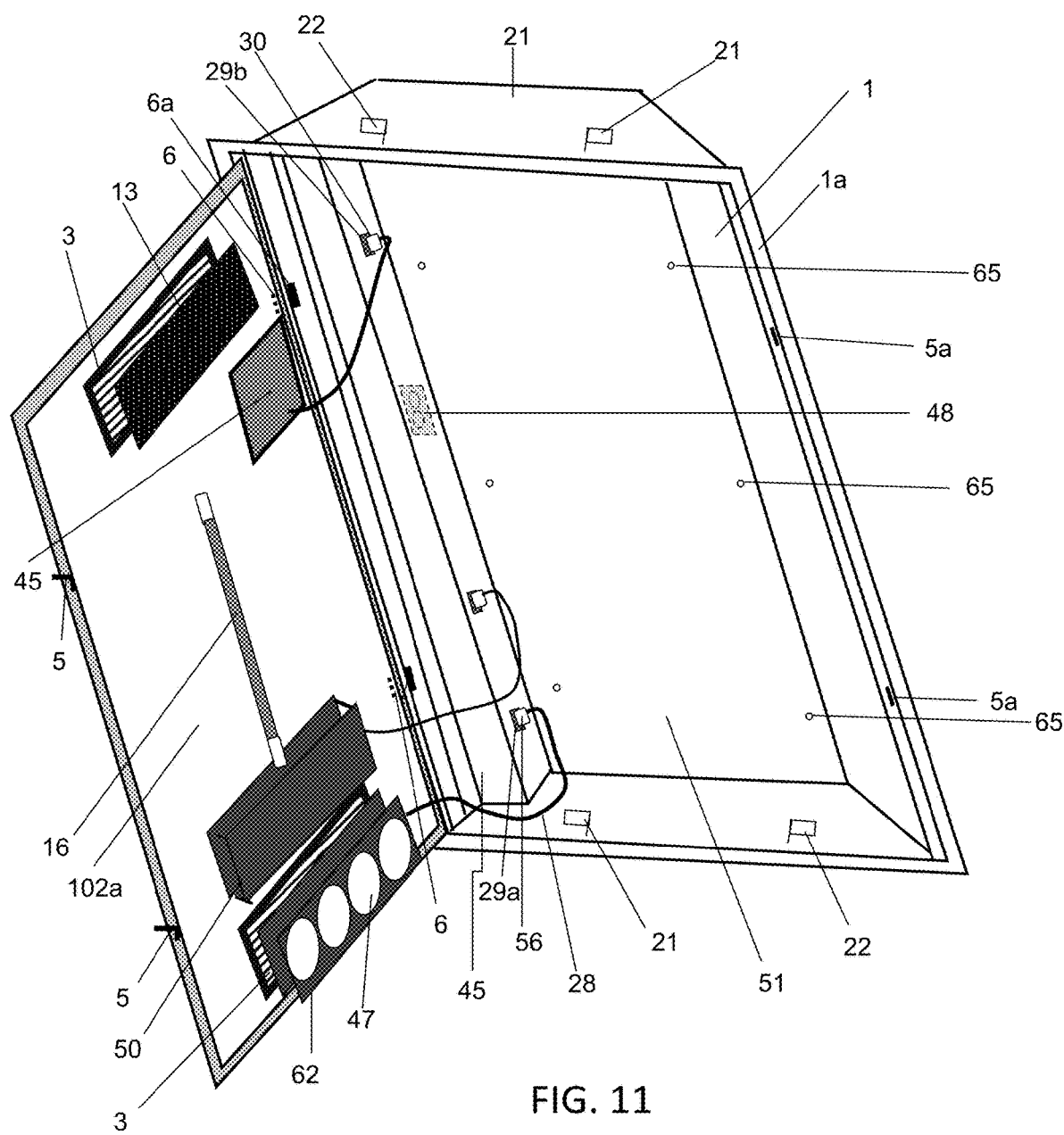
FIG. 11 is a front perspective view of the Ceiling-Mounted Decontamination Unit of the present invention showing alternate embodiment of FIG. 9 with Optional Full LED Panel Unit installed in open position and identified components.

With reference to FIGS. 7-9, the preferred embodiment for areas not requiring an installed luminaire, the housing 1 additionally includes hinge provisions 6a and latch provisions 5a to allow attachment or coupling of a drop ceiling tile 4 in hingable tile/lens frame 9.

In areas where luminaires are required, FIGS. 10-23 show the preferred embodiment of the ceiling-mounted decontamination unit hingable room luminaire 100. Alternate embodiments consist of hingable room luminaire 101, full size flat panel luminaire 102 with vents through panel and components mounted to rear of full-size flat panel unit, or other types of room luminaire capable of installing onto the housing 1 designed to illuminate a room. Hinge provision 6a and latch provision 5a are also capable of accepting lens 103 in hingable frame 9, which may consist of prismatic lens, flat lens, parabolic or other design capable of inserting or installing into the hingable tile/lens frame 9 and being securely returned to its closed position on housing 1 by way of the latch 5 and latch provision 25 located on the housing 1. The room luminaires 100, 101, and 102 are preferably selectively operable to illuminate the room or any environment where the ceiling-mounted decontamination unit is installed.

Additionally, FIGS. 2, 6-8, 11-12, 15, 17, 19-20, and 23 illustrate the housing 1 hinge provision 6a and latch provision 5a that allow for the attachment or coupling of a hingable Room Surface and Air Decontamination luminaire 104 for decontaminating room surfaces as well as air in a room that comes in contact with the external decontamination source 105.

Removable Maintenance Panel.

The housing 1 preferred embodiment includes at least one removable front internal air decontamination chamber maintenance panel 18 located on the internal decontamination cover 28. The internal air decontamination maintenance panel 18 can be opened and/or removed by way of maintenance panel attachment means on chamber 54 and attachment means on maintenance cover 53 from the lower center section of the air decontamination chamber 26 without the need to remove, dislodge, hinge, unhinge, pivot or in any way disengage the housing 1 from its mounted location on or onto the recessed ceiling grid or T-bar 37, as well as on or into a plaster or other non-recessed type ceiling 34b. The internal air decontamination chamber maintenance panel 18 is located on the room or floor side 36 of the decontamination chamber 26 and easily accessed from below the installed unit without disturbing the mounting position of the housing 1. Numeral 35 illustrates the area or open space in recessed/drop ceiling above an installed ceiling-mounted unit.

Access to the internal air decontamination chamber maintenance panel 18 requires disengaging the latches 5 on the hinged ceiling tile 4 (preferably in frame), room luminaires 100, 101, 102, prismatic lens (in frame) 103, or external room surface and air decontamination luminaire 104 (shown in open position 33) from the from the latch provision 5a on the housing 1. After disengaging the latches 5, the room luminaires 100, 101, 102, ceiling tile 4, prismatic lens in frame 103 or external room surface luminaire and air decontamination 104 open or hinge downward in the direction of the floor 36, preferably 90 degrees, to allow to allow access to the removable front air decontamination chamber maintenance panel 18 to remove or replace the decontamination source 16 located within the air decontamination chamber 15.

Physical Dimensions.

The physical dimensions of the housing 1 are nominally 2 foot in width by 4 foot (600 mm×1200 mm) in width being consistent with the size and physical specifications of known recessed type drop ceilings, grid ceiling, T-Bar Ceilings, Inverted T-Bar Ceilings, or other known ceiling types. Alternate size housings such as 2 foot by 2 foot (600 mm by 600 mm) and 1 foot by 4 foot (300 mm by 1200 mm). When installed into a recessed-type grid ceiling 34, the housing 1 size must be greater than the aperture or opening in the ceiling structure, ceiling grid system, or T-Bar 37 to prevent the housing 1 from dislodging or disengaging, either unintentionally or intentionally, from the unit's designed mounted position on the ceiling system. Physical size may vary depending on location standards and ceiling designs.

Mounting.

The preferred embodiment of the system and device of the present invention has a housing 1, including a flange feature 1a designed be directly positioned on, mounted to, resting on a recessed ceiling, grid ceiling, T-bar ceiling 37 or similar ceiling in a fixed, non-moveable, non-hinging, non-pivoting position, unable to be repositioned in any way after installation. The housing 1 is also designed for installation into or onto plaster ceiling, sheetrock ceiling, or other non-recessed type ceiling 34b and secured in a non-movable relationship with non-recessed ceiling structure.

The housing 1 is designed to be placed on, attached to, or mounted into or onto a recessed, suspended, grid, or drop ceiling, or room grid system in a room as well as into or onto a plaster ceiling, sheetrock ceiling, or other non-recessed type ceiling by permanently securing the housing 1 to the building structure by way of support provisions 55 on the housing 1 or end unit 21. Hole provisions 65 are provided in the housing 1 for direct or mechanical attachment of the housing 1 to non-recessed type ceiling by way of screws 68, bolts, rivets, anchors, clips, spring clips, fasteners, latches or other mechanical hardware or known means to secure unit to a non-recessed ceiling. An alternate embodiment of the housing includes provisions for installing a "unilug" or similar device designed to support recessing housing 1 into plaster ceilings or non-recessed ceilings.

Any combination of the disclosed attachment methods may be used, and the actual securing means such as tabs 55, integral hurricane clips 22, unilugs, or mechanical attachment used on the housing 1 determines the connection to the ceiling or surface (for example, bolts are bolted in and screws are screwed in—preferably into aluminum or wooden beams, or other structures that can support the weight of the ceiling-mounted decontamination unit). Hurricane clips in mounted position 33.

Internal Space.

The housing 1 has an internal space 1b, in which the internal components are mounted, including one or more internal air decontamination chamber 15 with decontamination source 16 and air deflectors 64 mounted within the chamber, intake vertical ducts 12a and exhaust vertical duct 12b for attaching means for driving air 47, preferably fan bracket 62 with fan bank 61 and fan power supply 63, filter 13, access plate for primary power supply connection 48, electrical raceway 40, electrical raceway cover 38, connectors for power supply to means for driving air 29a or fan power supply 63, hingable intake aperture 2a and hingable exhaust aperture 2b to mount vent grille covers 3, hinge provisions for hinge engagement 6a, slot provisions for latch engagement 5a, indicator lights 31, occupancy sensors 60, a door switch 66 to disconnect power when the system is opened, a drop ceiling tile 4 or ceiling tile in a hingable and detachable frame 9 designed to hinge open or detach from the housing 1 to access to the decontamination chamber 15 maintenance panel 18 for access to decontamination source 16 for maintenance or replacement. The housing 1 contains a power supply access plate 48 connected to the housing 1 for electrical supply connection from facility to system, which is positioned below the electrical raceway cover 38.

An alternate embodiment includes a power supply connector system 29a for means for driving air, power supply connector system 29b for optional room luminaire 100, 101, 102, external surface and air decontamination luminaire 104, LED Array Module Driver 46c, or other compatible room luminaires designs or decontamination systems.

Decontamination Source.

At least one internal decontamination source 16 is placed, attached or mounted into the decontamination chamber 15 located inside the internal space 1b of the housing 1. Also contained in the internal space 1b of the housing 1 are the means for driving air 47 through the decontamination chamber 15, wherein the air is decontaminated by the at least one internal decontamination source 16, mounted in a direction parallel with air moving through the chamber to maximum exposure time with air moving through the chamber 15. The means for driving air 47 are preferably air fans, but they could be other means for driving air. Thus, the reference to the means for driving air 47 take room air into the internal space 1b of the housing 1, through the intake aperture 2a, through vertical duct 12a and drive it into the decontamination chamber 15. When the at least one internal decontamination source 16 is active, pathogens such as bacteria, virus, or other microorganisms that can cause disease, are killed or disabled when passing through the decontamination chamber 15.

The means for driving air 47 then exhaust decontaminated air 20 from the decontamination chamber 15 in the internal space 1b of the housing 1 through the exhaust vertical duct 12b, passing the exhaust aperture 2b before returning the decontaminated air 20 directly back to the room. The means for driving air 47 may include optional air filters 13, such as, for example particular matter filters or other known filters. The directional arrows 19 show the path of air flow that comes into the intake aperture 19, through the Intake Vertical Duct 12a and the directional arrows 14 show the path of the air 14 flows through the decontamination chamber 15 making direct contact with the decontamination source 16 as the decontaminated air 20 travels through the Exhaust vertical Duct 12b that comes out of the exhaust aperture 20. The directional arrows 14 show the path of traveling across perpendicular air deflectors 64 designed to create a stirring and swirling effect that causes an unsteady movement of air through the decontamination chamber 15. The intake aperture 2a and exhaust aperture 2b are hinged and removable or hinged to enable easy access to the air filters 13 for maintenance and/or replacement.

Figure 5:
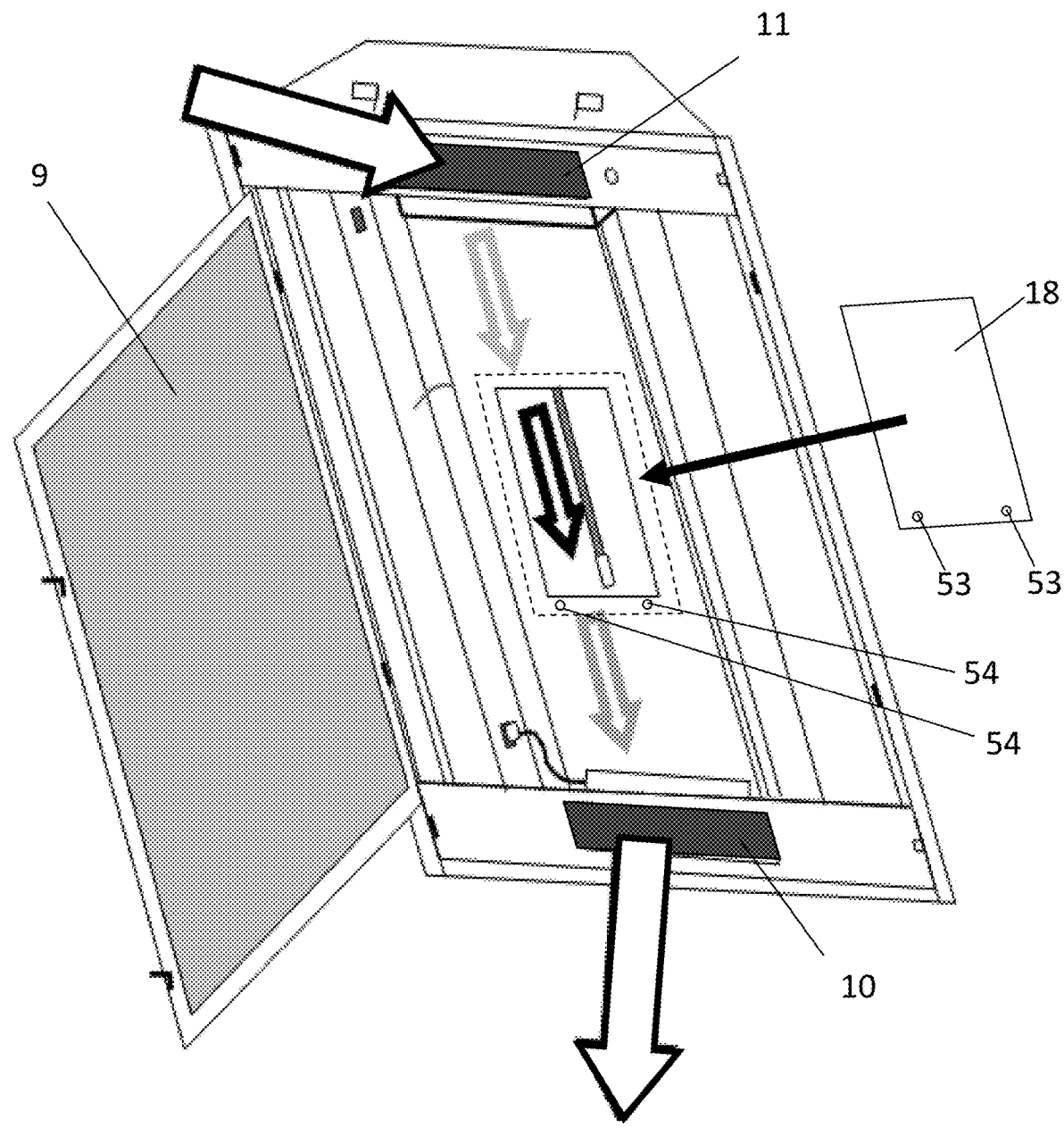
FIG. 5 is a front perspective view of the Ceiling-Mounted Decontamination Unit with alternate embodiment of FIG. 1 with Optional Room Luminaire in open position showing identified components and vent grille covers removed from intake and exhaust apertures.
Figure 6:
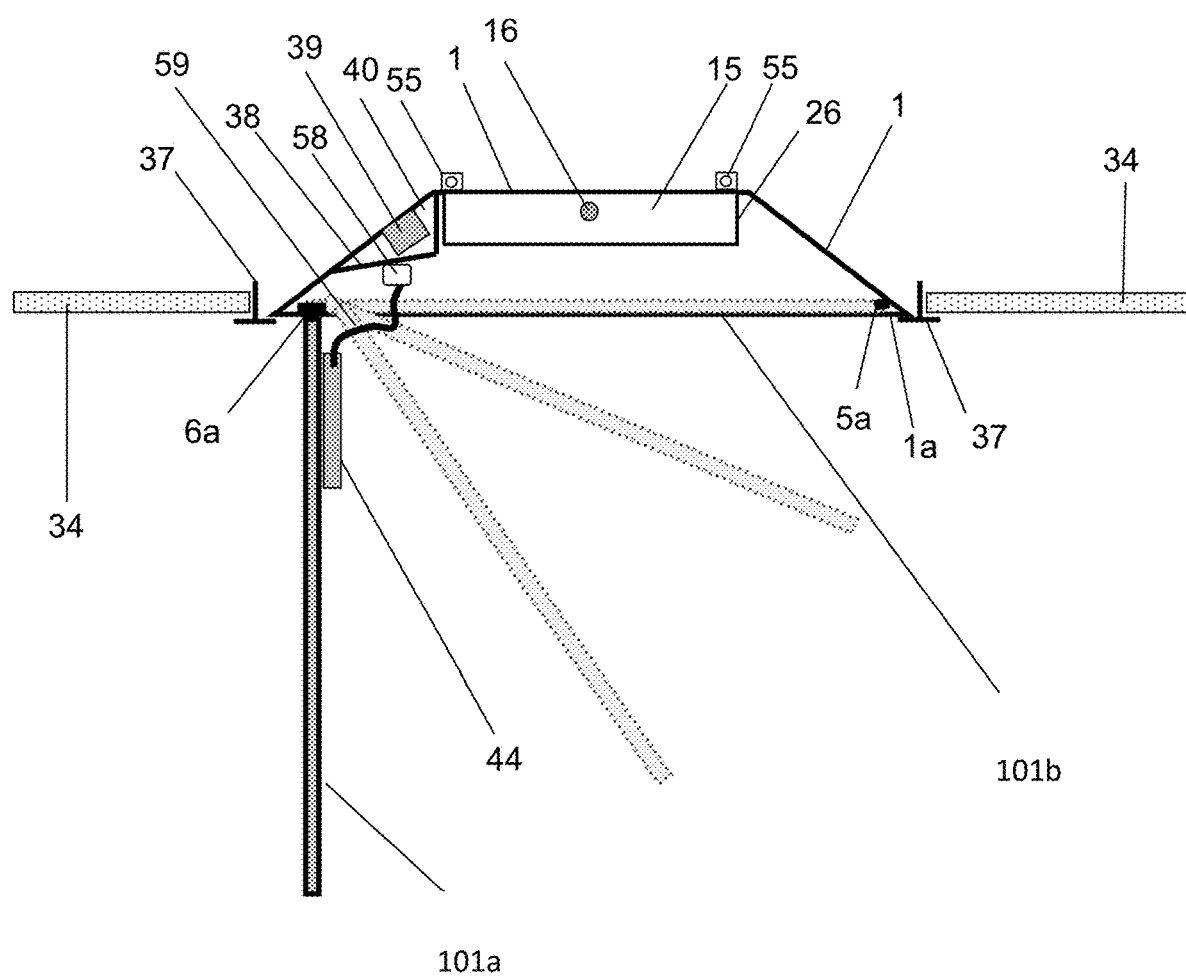
FIG. 6 is an end view of the Ceiling-Mounted Decontamination Unit with alternate embodiment of FIG. 1 with Optional Room Luminaire option and identified components.
Figure 12:
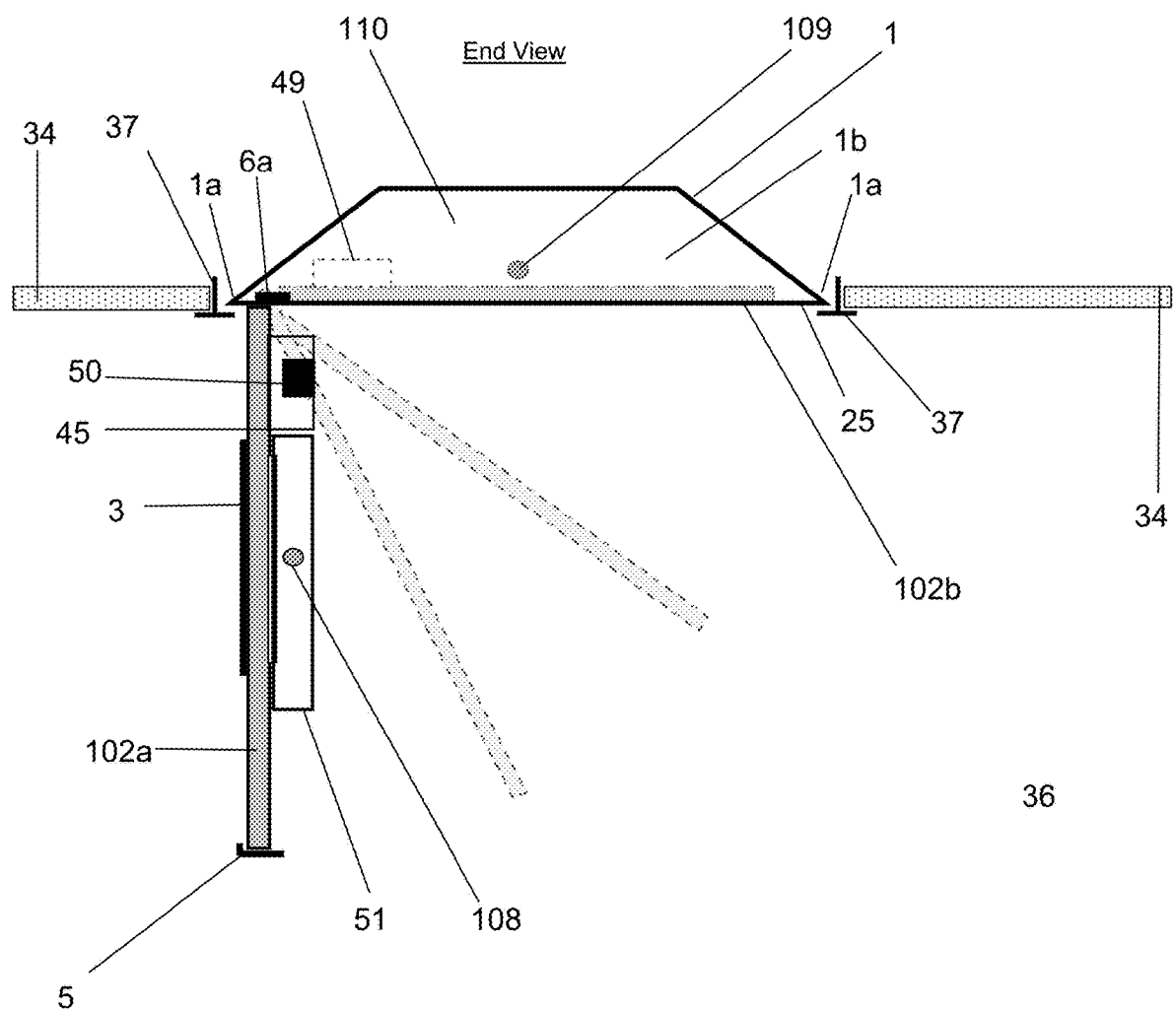
FIG. 12 is an end view of the Ceiling-Mounted Decontamination Unit in present invention showing alternate embodiment of FIG. 9 with identified components.
Figure 13:
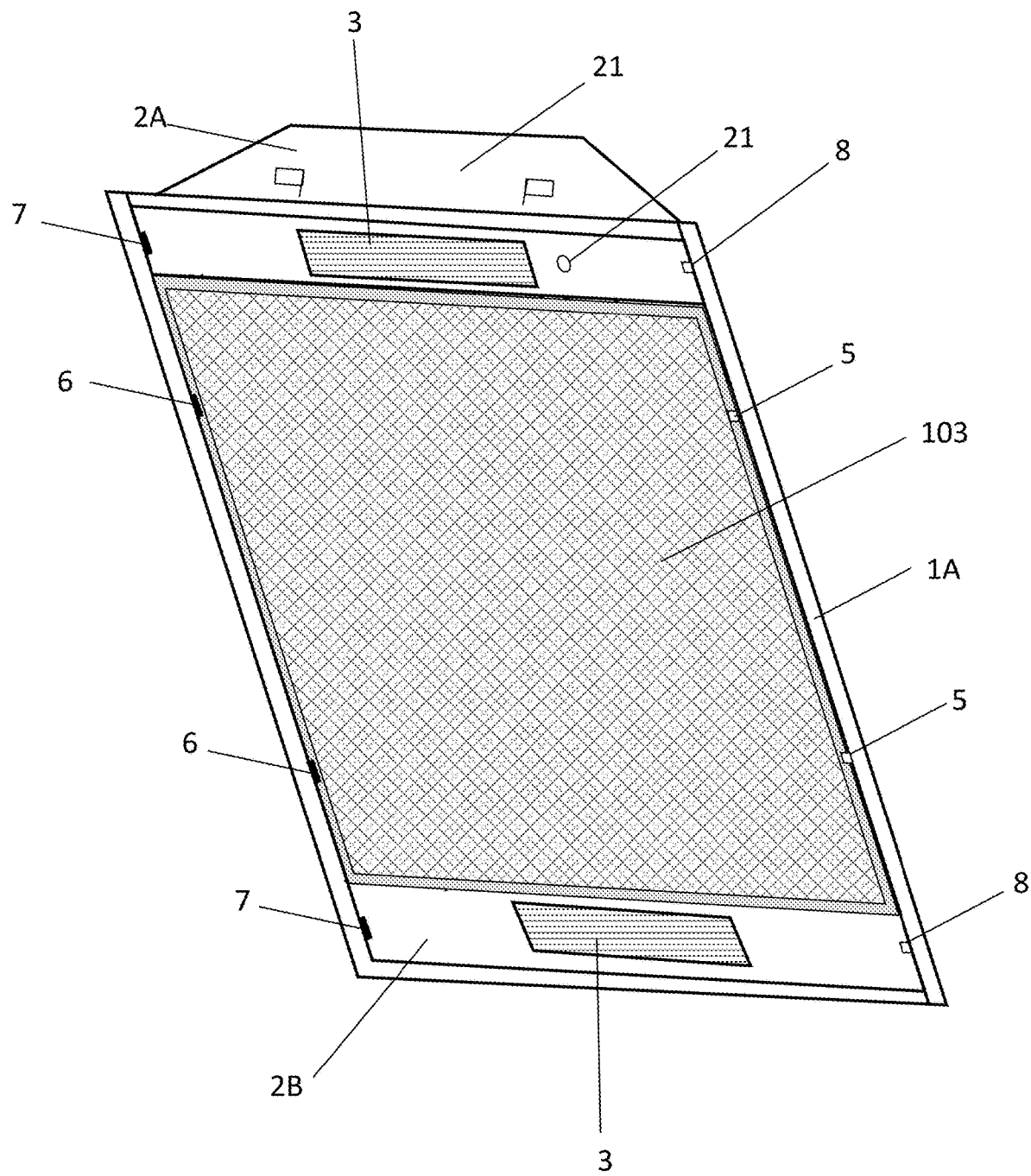
FIG. 13 is a front perspective view of the Ceiling-Mounted Decontamination Unit of present invention showing alternate embodiment of FIG. 13 with Optional lens in frame and LED Array with identified components.
Figure 14:
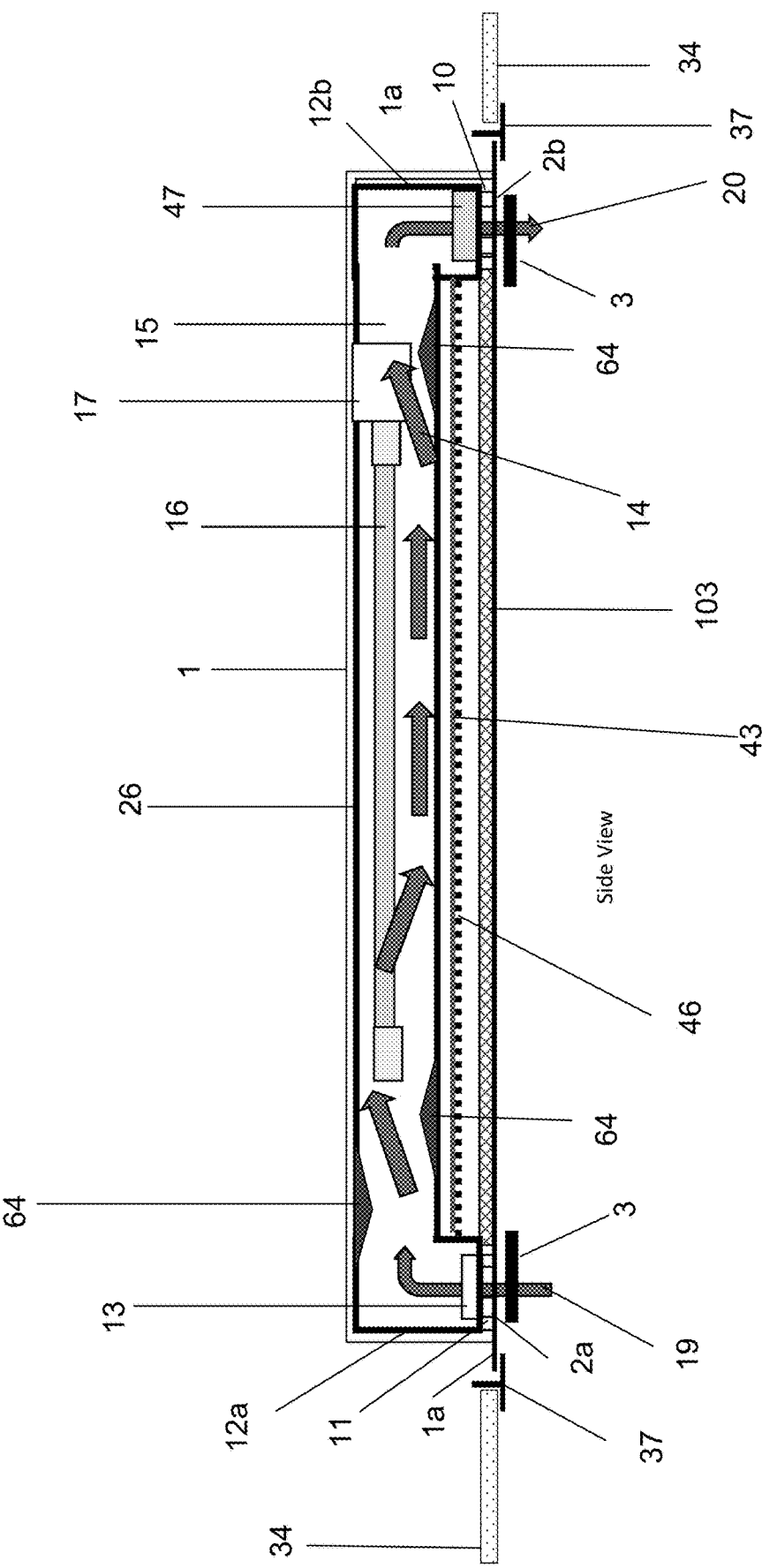
FIG. 14 is a side view cross section of the Ceiling-Mounted Decontamination Unit of present invention with alternate embodiment of FIG. 13 showing air path and identified components.
Figure 15:
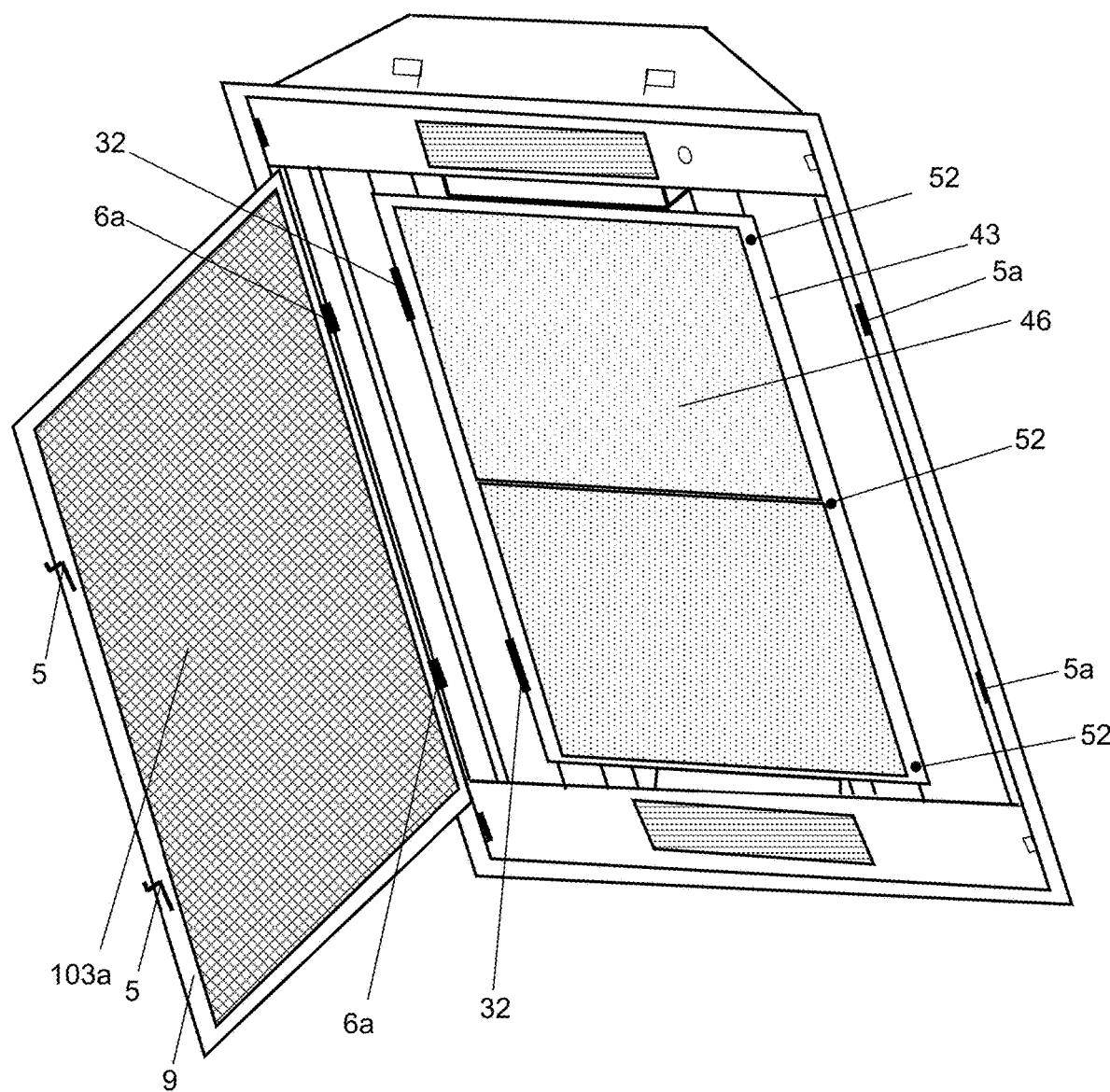
FIG. 15 is a front perspective view of the Ceiling-Mounted Decontamination Unit of present invention showing alternate embodiment of FIG. 13 with identified components.
Figure 16:
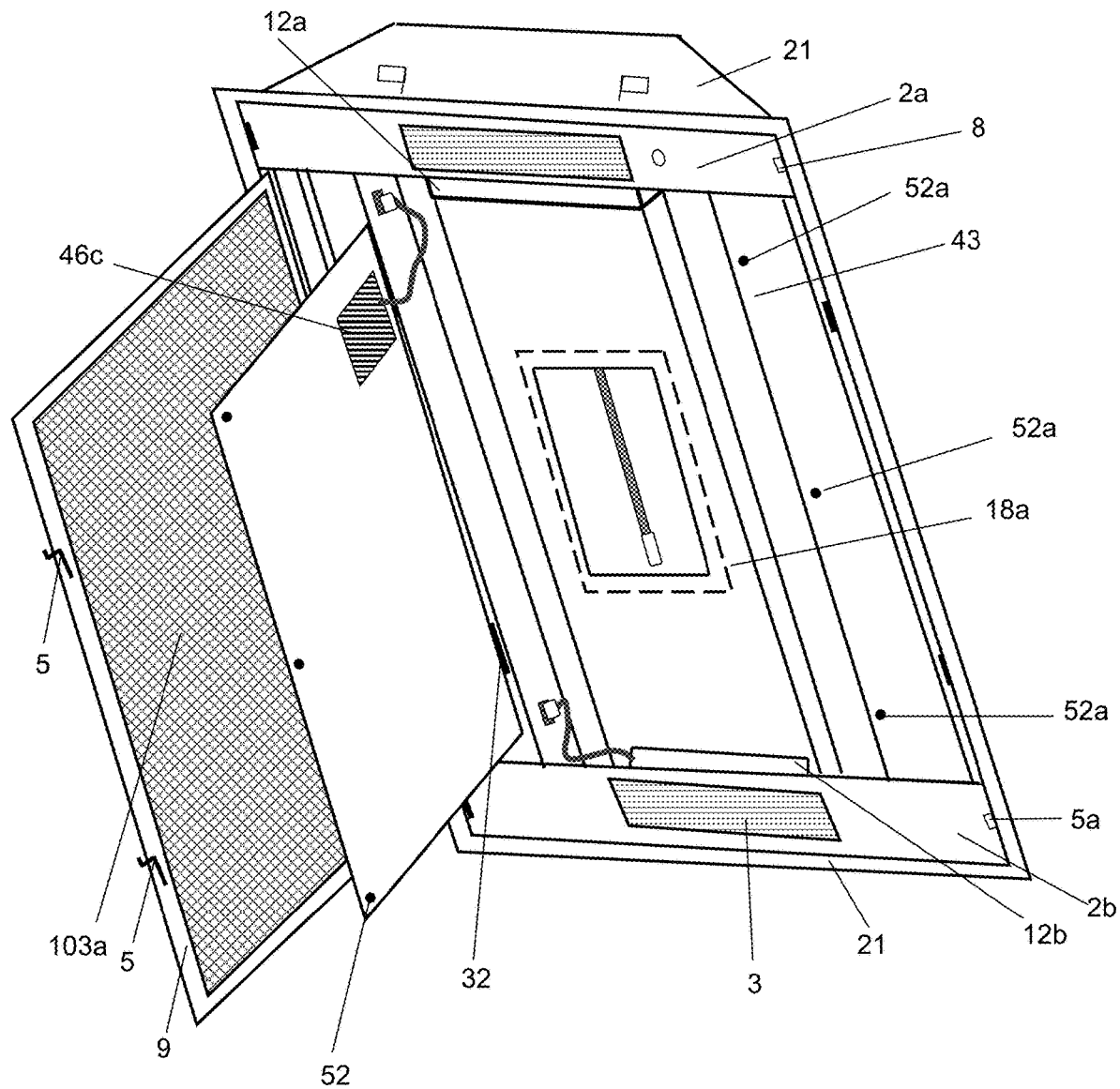
FIG. 16 is another front perspective view of the Ceiling-Mounted Decontamination Unit of present invention showing alternate embodiment of FIG. 13 with identified components.
Figure 17:
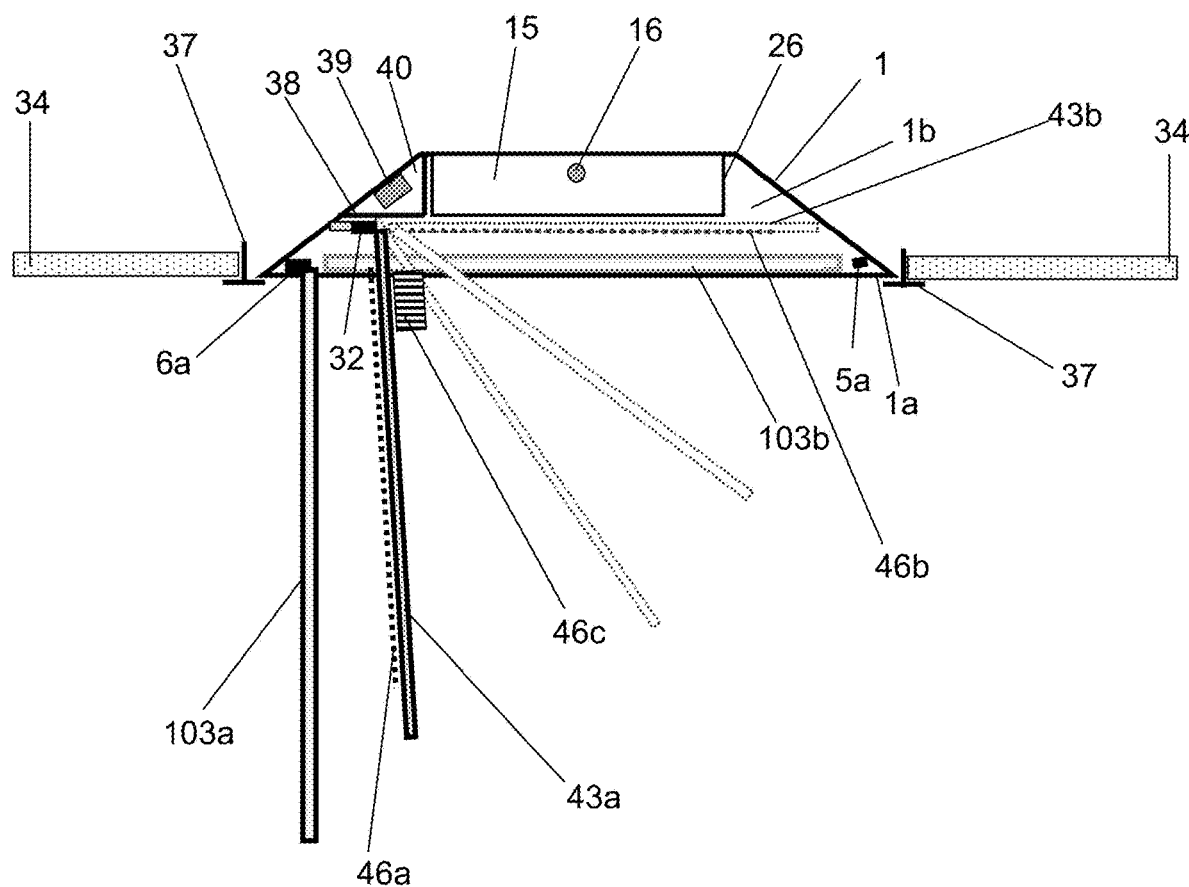
FIG. 17 is an end view of the Ceiling-Mounted Decontamination Unit in present invention showing alternate embodiment of FIG. 13 with identified components.
Figure 18:
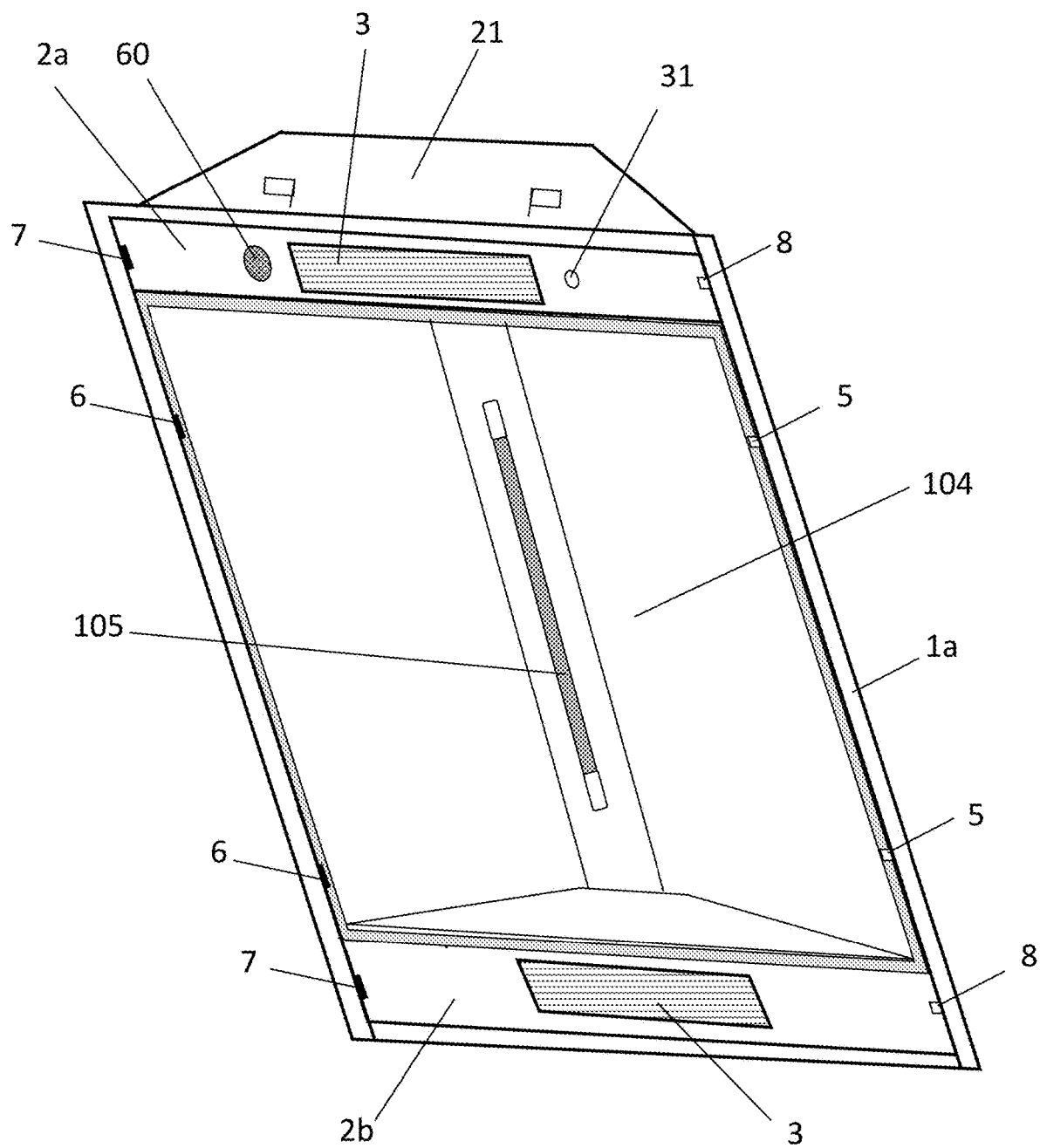
FIG. 18 is a front perspective view of the Ceiling-Mounted Decontamination Unit of present invention showing alternate embodiment with installed Optional Room Surface and Air Luminaire with identified components.
Figures 19, 19A:
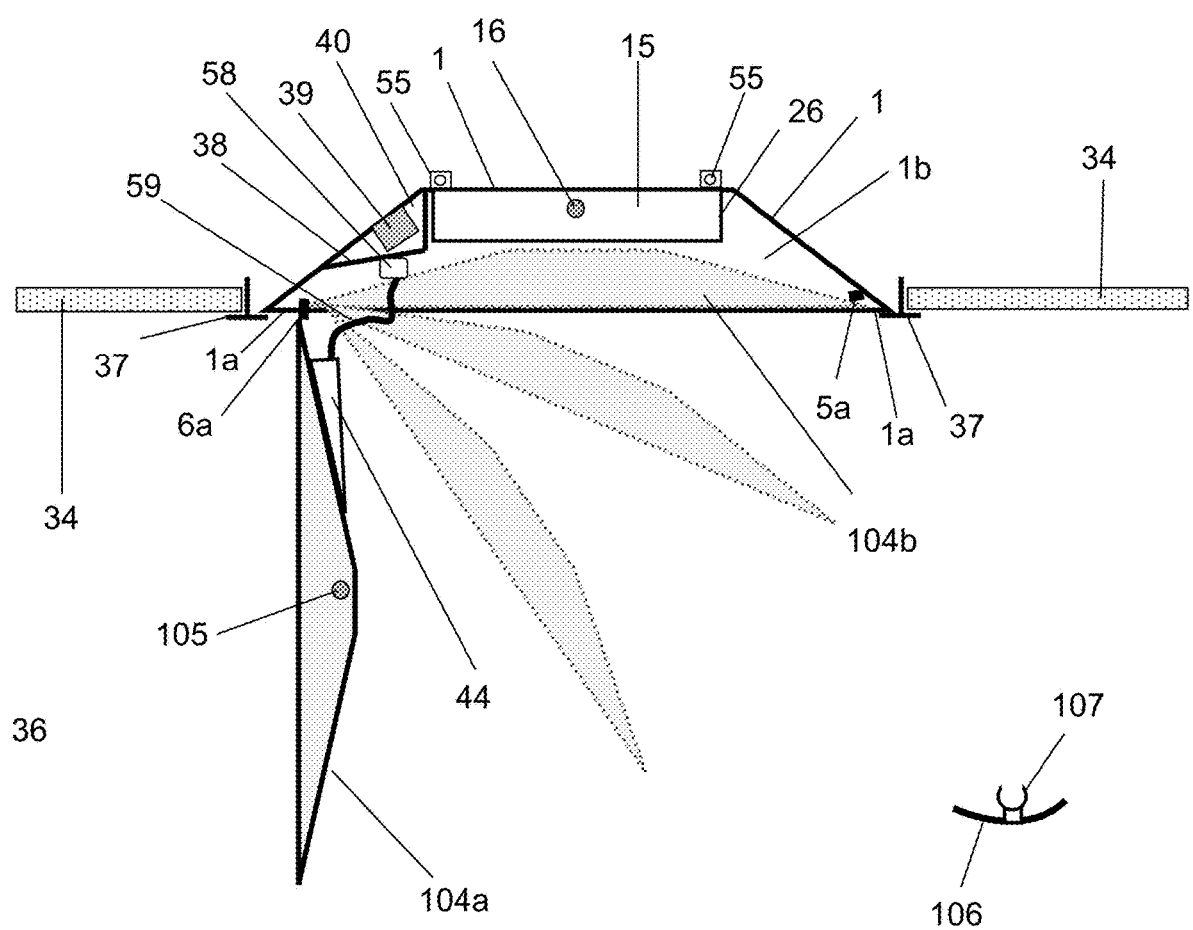
FIG. 19 is an end view of the Ceiling-Mounted Decontamination Unit of present invention showing alternate embodiment of FIG. 18 with identified components.
Figure 20:
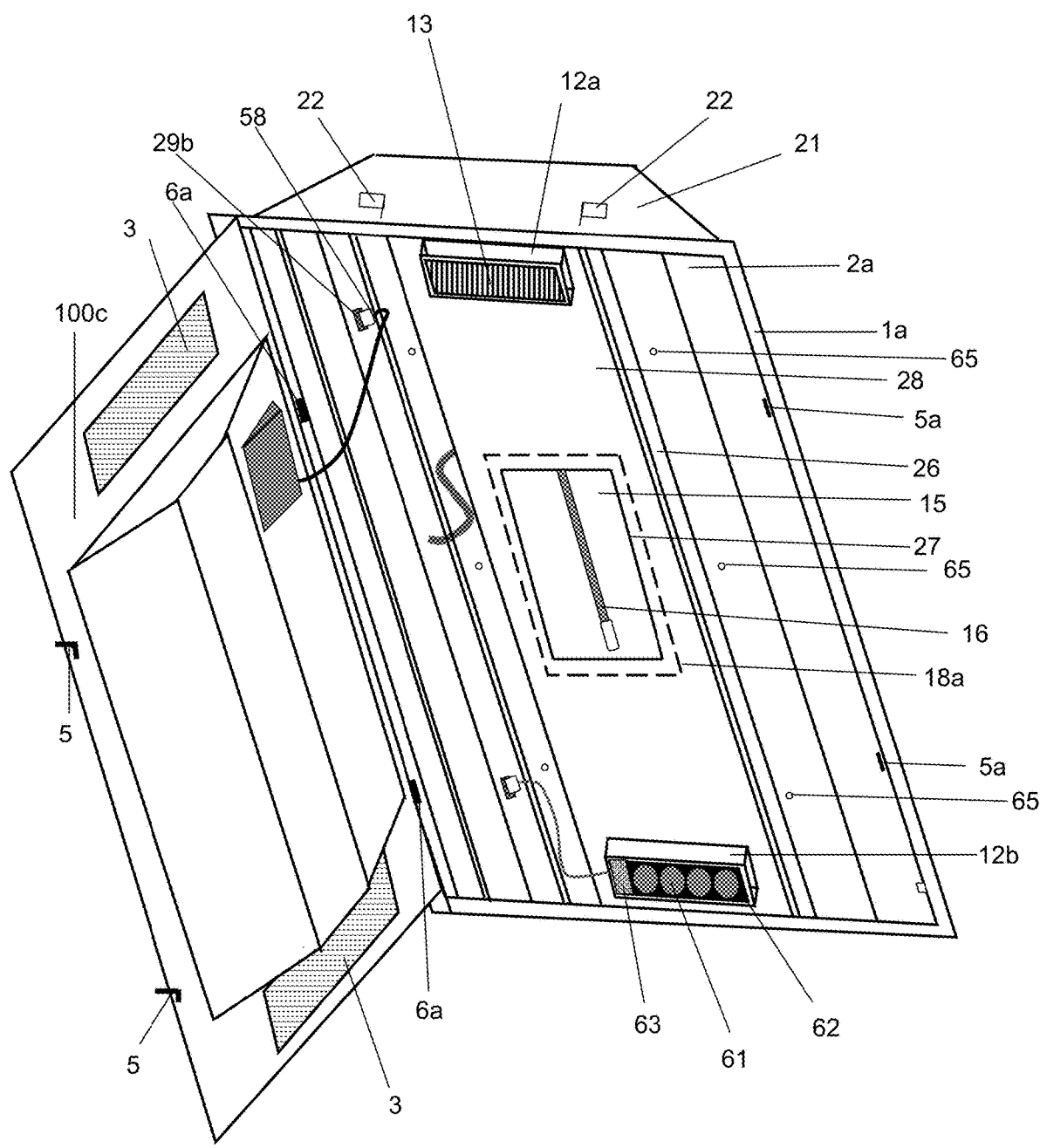
FIG. 20 is a front perspective view of the Ceiling-Mounted Decontamination Unit of present invention showing an alternate embodiment of FIG. 4 with Room Luminaire, Intake Aperture, and Exhaust Aperture combined on single surface with identified components.
Figure 21:
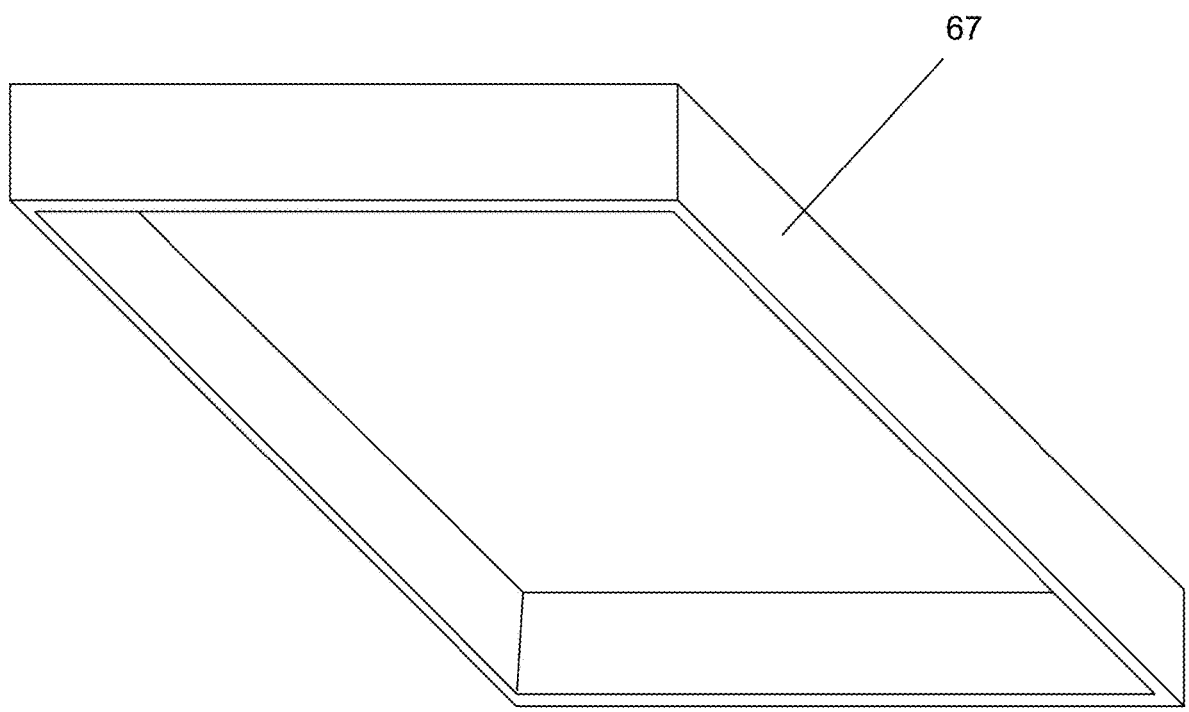
FIG. 21 is a perspective view of the Ceiling-Mounted Decontamination Unit of present invention decorative surface mount trim component.
Figure 22:
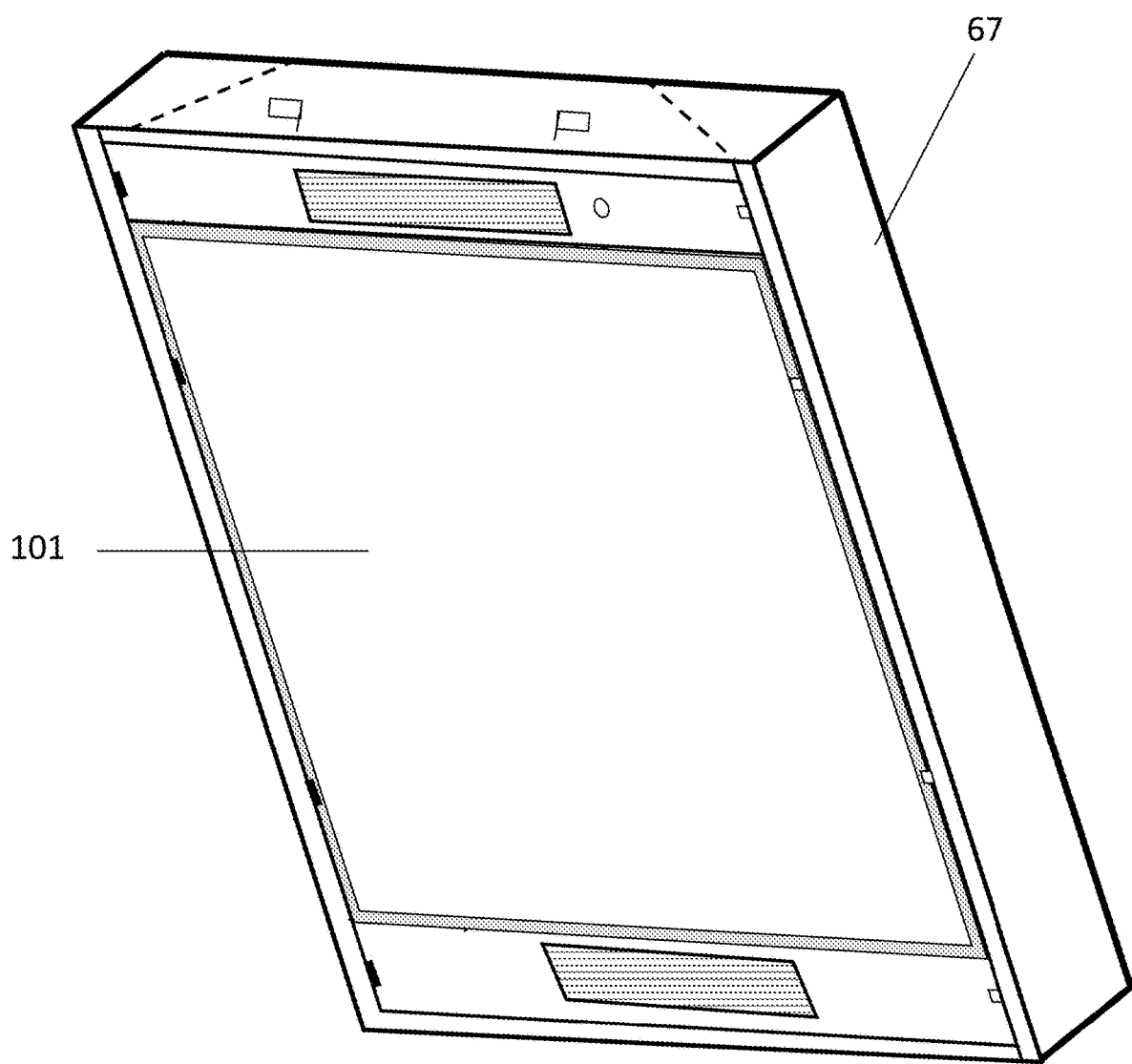
FIG. 22 is a perspective view of the Ceiling-Mounted Decontamination Unit of present invention showing alternate embodiment of FIG. 5 with decorative surface mount trim component installed.
Figure 23:
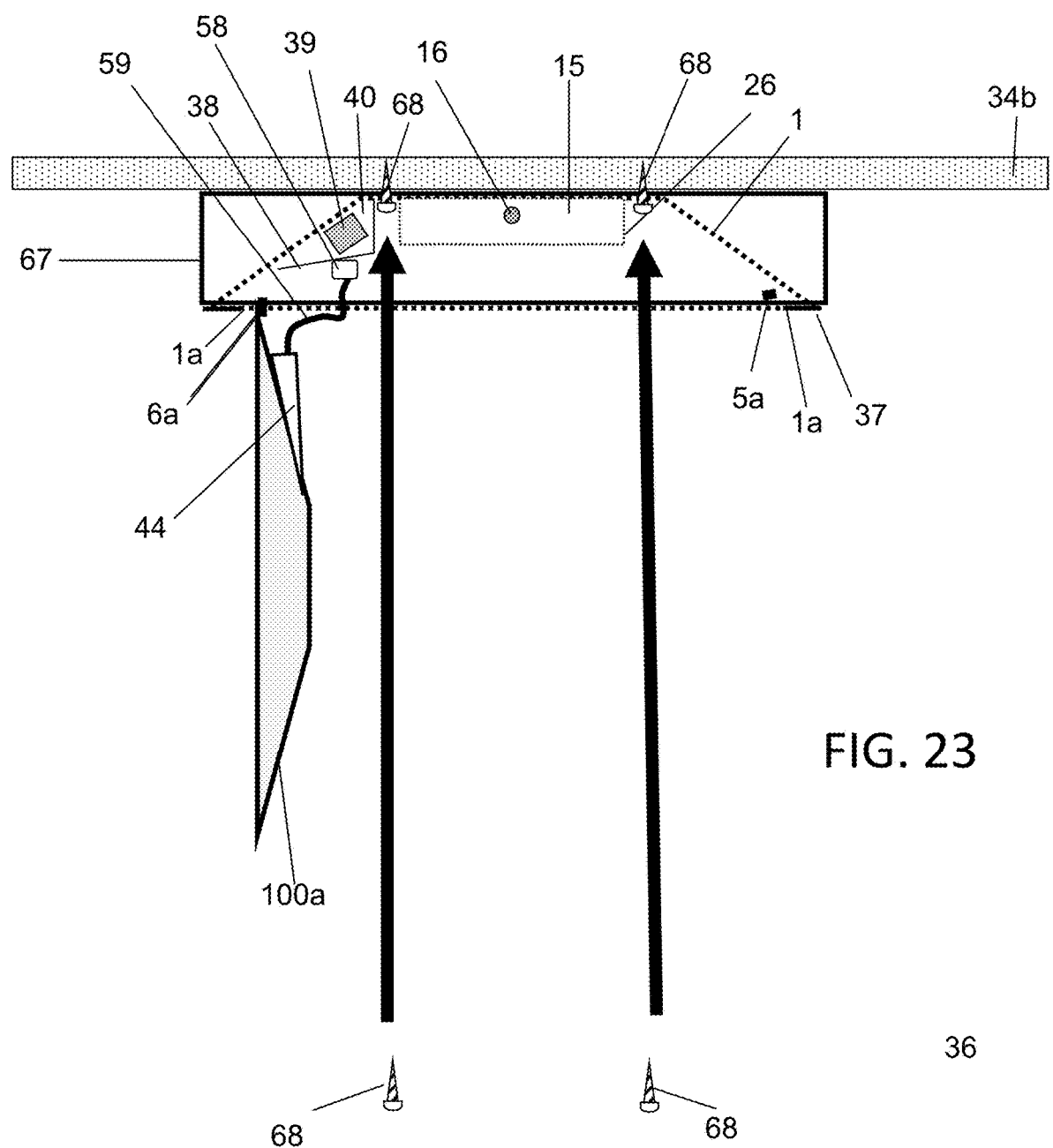
FIG. 23 is an end view of the Ceiling-Mounted Decontamination Unit of present invention decorative surface mount trim component with identified components.

FIG. 12 shows designed maintenance features intake aperture in open position 2c, to allow service for filter and exhaust aperture in open position 2d for access to means for driving air 47 or fan bank 61. FIG. 5 shows intake aperture design 11 and exhaust aperture design 10 with indicator light knockout 24 and room occupancy sensor knockout 25 provisions when needed.

The housing 1 preferably includes a drop ceiling tile 4 or ceiling tile, in a hingable and detachable frame 9, designed to open downwardly, in a direction the room floor 36, to allow access to the maintenance panel 18 located on the maintenance panel 18a to allow access to the decontamination chamber 15 located within the housing 1 internal space 1b. The decontamination source 16 is connected to the decontamination source provision 17 which exits the side of the decontamination chamber base 26 by way of connecting cable 30

Alternate embodiments of the ceiling-mounted decontamination unit include a hingable and detachable room luminaire 100, 101, 102, hingable and detachable external surface and air decontamination luminaire 104, hingable and detachable LED Array Module Driver 46c, or other compatible room luminaires designs or decontamination systems with similar removable or hinging features. Room luminaires are designed to hinge open to allow access to the maintenance panel 18 located in the housing 1 internal space 1a.

Optional attachment to the ceiling-mounted decontamination unit are designed to attach, couple, secure to the housing by way of hinge device 6 and latch device 5 and pluggable connection cord to be easily removable, tool-free, for maintenance, replacement, of interchanged. Hingable ceiling tile 4 in installed closed position 41 hinges open 90 degrees 42. Room Luminaire 100 (FIG. 4 and FIG. 7), shown in open position 100a and closed position 100b (FIG. 8 and FIG. 23), single piece luminaire including intake and exhaust apertures shown in open position 100c (FIG. 20), and Room Luminaire 101 (FIG. 22), shown in open position 101a and closed position 101b (FIG. 6), are self-contained with luminaire power supply 44 attached directly to the hingable luminaire connected by cord 59 with male connector/plug 58 inserting into female connector 29 which is secured to electrical raceway 40 and cover 38.

Room Luminaire 102 (FIGS. 9-12) is shown in open position 102a and closed position 102b with electrical enclosure 45 (open position 49 and closed position 50) with housing 1 internal space providing decontamination base for internal decontamination chamber 110, shown open 51, with air decontamination source in open position 108 and closed position 109. Room Luminaire 103 (FIGS. 13-17), shown in open position 103a and closed position 103b. External Room Surface and Air Decontamination Luminaire 104 (FIGS. 18-19) with external decontamination source 105, shown in open position 104a and closed position 104b with UV Shield (FIG. 19a) 106 and 107 designed to block the UV rays when for using Ozone only. For surface mounting the ceiling-mounted decontamination unit, a decorative trim 67 is available for a finished surface appearance.

For room luminaire attachment utilizing lens in from 103 an LED Array panel 46, is mounted to a hingable panel 43, shown in open position 46a and closed position 46b, using mounting provisions 52 on LED array panel and 52a provision in housing 1, is mounted to a hingable surface 43 which opens 43a by way of an internal set of hinge provisions 32a and hinges 32 to access maintenance panel 18 and mounting provisions 52 and 52a to be mechanically fastened to housing 1 to a secure closed position 43b.

The ceiling-mounted decontamination unit includes air intake aperture 2a and air exhaust aperture 2b include provisions to mount vent grill covers 3 with hinge feature 7 designed to be opened by way of latch feature 8 to allow access to means for driving air 47 or fan bank 61 and filters 13.

Means for driving air 47 or fan bank 61 including Fan Power Supply 63 is modular, contains a power cord 57 and connecting plug 56 designed to plug directly into power supply connection 29a positioned in housing internal space 1b, located preferably on electrical raceway cover 38. Means for driving air 47 or fan bank 61 are designed to be accessible by way of hinged air intake aperture 2a or air exhaust aperture 2b and easily removed from mounted position in a tool-free manner.

The Recessed Ceiling and Surface Decontamination System may have a back-up (battery or rechargeable battery) power supply in case of a power for power to the attached room luminaires 100, 101, 103 and 105 in the event of a power failure. Optional Emergency back-up source will be installed within the housing electrical raceway 40.

The ceiling-mounted decontamination unit attached room luminaire 100, 101, 103, and 105 may include wiring and provisions for dimming or known lighting control capabilities While the system and device of the present invention have been shown and described in accordance with the preferred and practical embodiments thereof, it is recognized that departures from the instant disclosure are contemplated within the spirit and scope of the present invention. Therefore, the true scope of the invention should not be limited by the abovementioned description of the preferred embodiment since other modifications may become apparent to those skilled in the art upon a study of the drawings, description, explanations, and specifications herein. Various modifications to these embodiments will be readily apparent to those skilled in the art, and the principles described herein can be applied to other embodiments without departing from the spirit or scope of the invention and the subject matter of the present invention.

Installation Facilities.

The system and device of the present invention may be used not just in offices, hospital, health care facilities but also other locations with increased likelihood of bacteria or other pathogen accumulation, such as any common area where people congregate or spend time, public places, buses, airports, aircraft, spacecraft, ships, emergency vehicles, transportation vehicles, or any other area with a particular emphasis on sanitary facilities or decontamination.

Additional Operational Concepts.

A ceiling-mounted decontamination unit housing with the following elements:

Ceiling Types
a. A housing, defining an internal space, said housing placed, attached, installed directly onto or into a recessed drop ceiling, grid ceiling, suspended ceiling, T-Bar ceiling, Inverter T-Bar ceiling or similar known recessed ceiling type as well as recessed into or onto a plaster or sheetrock ceiling or other known non-suspended type ceiling inside a room or space;

Non-Movable-Pivoting-Hinging Housing
b. A housing designed of proper physical dimensions, greater than the drop ceiling aperture or opening, to install permanently onto and remain in constant contact with the recessed ceiling grid in a non-movable, non-pivoting, non-hinging, or other type of known repositioning relationship with recessed drop ceiling, grid ceiling, suspended ceiling T-Bar ceiling, Inverter T-Bar ceiling or similar ceiling as well as plaster or other non-recessed type ceiling;

Provisions for Support to Ceiling
c. A housing designed with provisions for ceiling support, hanger wires, or other known support devices designed to provide additional support to the installed device housing in the recessed ceiling grid or plaster ceiling to prevent movement or dislodging of the device in any way after installation;

Hurricane Clips on Housing
d. A housing consisting of hurricane clip feature built into the housing and end support tabs, both are built into the device end designed to pry, bend, or be positioned away from housing to engage directly with recessed ceiling grid or support means directly attached to the installation facility or structure to prevent the housing from dislodging, moving, or disengaging in any way from the installed position;

Recessed or Ceiling Mount Provisions
e. A housing designed to mount permanently onto or into a recessed drop ceiling grid as well as non-recessed ceiling including mounting holes in the housing that are accessible outside the air flow path and chamber, to mechanically secure the housing to a non-recessed or plaster/sheetrock ceiling in a way that does not require attachment means to utilize, enter, go through, or breach the decontamination chamber or air flow area in any way;

Air Decontamination System
f. An internal space disposed in Recessed Ceiling or Surface Decontamination System internal space, defining an air decontamination chamber, duct, space, channel, or raceway therebetween;

Decontamination Source in Chamber/Duct
g. At least one internal decontamination source adapted to be placed, attached or mounted into the ceiling-mounted decontamination unit air decontamination chamber, duct, space, channel or raceway;

Means for Driving Air
h. Means for driving air through the air decontamination internal chamber, duct, space, channel or raceway;

Air Intake and Exhaust Apertures
i. Housing contains at least one air intake aperture that draws room air into the air decontamination chamber and one exhaust aperture that exhausts the decontaminated air from the decontamination chamber, directly back into the same room below, without additional duct, ductwork, or provisions;

Filter and Means for Driving Air Attached to Intake and Exhaust Apertures
j. Housing intake and exhaust apertures have provisions for mounting, placing, adapting, or installing a means for driving air as well as an air filter;

Air Intake and Exhaust Apertures Reversible
k. Housing contains provisions that allow the means for driving air to be easily reversed allowing the means for driving air to be located on the intake aperture to push the air through the internal chamber, or to be mounted on the exhaust aperture and pull the air through the internal chamber;

Air Intake and Exhaust Aperture Cover, Grill or Air Vent Diffuser
l. Housing contains at least one cover, grill, or air vent diffuser to be mounted at the intake aperture as well as one to be mounted at the exhaust aperture to provide desired direction and assist the air entering and existing the Air Decontamination System within the housing;

Hingable Air Intake and Exhaust
m. Housing contains a hingable or removable air intake aperture and exhaust aperture designed to hinge open, allowing access to the system's means for driving air as well as filter for maintenance. A latch provision located on the housing secures the hingable intake aperture and exhaust aperture to the housing during operation;

Means for Attaching Center Ceiling Tile, Luminaire or Surface Decontamination Unit n. A housing with hinge and latch provisions to mechanically attach a hingable, opening, or pivoting-type device such as a ceiling tile (in frame), room luminaire, room surface and air decontamination luminaire or other device compatible hinge and latch system, directly to the housing without the need for additional brackets or other devices. Devices such as ceiling tile in frame, room luminaire, and room surface and air decontamination luminaire are designed to hinge open and close as well as be easily removed from the system without tools;

Variety of Hingable Room Luminaire and Room Air/Surface Luminaires Available o. The housing includes hinge and latch provisions that allows for intake aperture, exhaust aperture, along with Ceiling Tile in Frame, Room Luminaire, or Room Surface and Air Decontamination Luminaire to open together as a single unit or independently to allow full or partial access to the housing internal space and components;

Air Decontamination Source—Access Panel p. Housing contains at least one maintenance panel in the air decontamination chamber or duct located on the room side or lower surface of installed unit; and/or Power Supply Connection q. Housing contains power supply connection for means for driving air and Room Luminaire, and Room Surface or Air Decontamination Luminaire located in or on the electrical raceway cover utilizing a connecting system that is compatible with the connector located on the means for driving air, Room Luminaire, or Room Surface and Air Decontamination System.

Decontamination Source in Chamber (Direct Contact with Air)

2. The decontamination system of concept 1, wherein the least one internal decontamination source is placed, attached or mounted into the air decontamination, chamber, duct, or space positioned parallel with the in air path in the chamber, directly in contact with the air moving through the chamber, duct, space, channel or raceway for decontamination.

Intake Aperture

3. The Recessed Ceiling or Surface Germicidal Decontamination System of concept 1, further comprising at least one hingable and removable air intake aperture, located on the housing, cooperating with the means for driving air into the decontamination chamber or the filter. Hingable Intake aperture is designed to hinge open to grant access to the means for driving air or filter for maintenance.

Exhaust Aperture

4. The Recessed Ceiling or Surface Germicidal Decontamination System of concept 1, further comprising at least one hingable and removable air exhaust aperture, located on the housing, cooperating with the filter or means for driving air out of the decontamination chamber and directly back into the room. Hingable exhaust aperture is designed to hinge open to grant access to the means for driving air or the filter for maintenance.

Direct Contact with Recessed Ceiling Grid

5. The Recessed Ceiling or Surface Decontamination System of concept 1 is in direct and permanent contact with the room ceiling grid or T-bar as the housing completely closes off the ceiling aperture or opening in a way that does not expose the room below to contaminants in the plenum or area above the installed unit at any time.

Maintenance Panel in Duct

6. The Recessed Ceiling or Surface Decontamination System of concept 1, further comprising a maintenance panel on the decontamination chamber to access the decontamination source for maintenance and replacement.

Filter at Intake or Exhaust

7. The Recessed Ceiling or Surface Decontamination System of concept 1, further comprising at least one air filter positioned at hingable intake aperture or exhaust aperture coupled with the means for driving air, accessible by way of opening the hingable intake aperture or exhaust aperture without disengaging the housing from its mounted position.

Tool Free Maintenance

8. The Recessed Ceiling or Surface Decontamination System of concept 1, wherein one or more ceiling tile in frame, room luminaire, room surface and air decontamination luminaire, filter, and the means for driving air are modular, are designed for tool-free installation, removal, and replacement.

Decontamoination Source for Air Chamber

9. The Recessed Ceiling or Surface Decontamination System's Air Decontamination Source located within the air decontamination chamber of concept 1, is designed to destroy pathogens in room air where the Recessed Ceiling or Surface Decontamination System is installed. The at least one decontamination source is selected from a group consisting of germicidal light, ultraviolet light, ultraviolet-C light (UV-C), ozone, sonic source, and ultrasonic source or other known decontamination source.

Decontamination Source for Room Surface and Air Luminaire

10. The Recessed Ceiling or Surface Decontamination System's Decontamination Source associated with the Room Surface and Air Decontamination Luminaire of concept 1, is designed to destroy pathogens in rom air where the Recessed Ceiling or Surface Germicidal Decontamination System is installed. The at least one decontamination source is selected from a group consisting of germicidal light, ultraviolet light, ultraviolet-C light (UV-C), ozone, sonic source, and ultrasonic source or other known decontamination source. The room surface and air decontamination luminaire contains attached hinges and latches that are compatible with the hinge and latch provisions installed in system housing.

Room Luminaire Occupancy Sensor or Battery Backup

11. One or more luminaires connected to the Recessed Ceiling or Surface Decontamination System in a hinge/pivot and latch, or other similar known means, relationship is selectively operable to illuminate the room and may contain an occupancy sensor or emergency backup power supply or battery in the event of a power failure. The Room Luminaire is self-contained with components attached to luminaire and designed to hinge, pivot, or open downwardly toward the floor and disengage or disconnect in a tool-free manner from the Recessed Ceiling or Surface Germicidal Air Decontamination System housing for maintenance or replacement.

Recessed, Non-Recessed, or Surface Mounted

12. A Recessed Ceiling or Surface Decontamination System, comprising:

j. A housing having an intake aperture and exhaust aperture, with air decontamination chamber defining an internal space therebetween, said housing adapted to be placed, attached, or other means related to the unit in direct contact with recessed ceiling grid, Inverted T-bar Ceiling, T-bar Ceiling, suspended ceiling, or other known recessed-type ceilings. The housing is also designed to be directly mounted into or onto a plaster ceiling or other known non-recessed-type ceilings;

k. A self-contained, Room Luminaire, selectively operable to illuminate the room, with power connection means compatible with power supply mating connector located on housing, coupled with the housing, designed to be hingable, removable, and detachable tool-free maintenance or replacement;

l. A self-contained, Room Surface and Air Decontamination Luminaire selectively operable to decontaminate surfaces and air in the area where unit is installed, with power connection means compatible with power supply mating connector located on housing, coupled with the housing, designed to be hingable, removable, and detachable tool-free maintenance or replacement;

m. A means for driving air that is modular and/or interchangeable to allow the means for driving air, power supply for means for driving air, and all associated components to be grouped together in a single assembly, compartment, bracket, or similar provision with attached cord and plug connector compatible with the housing electrical raceway mating connector for easy for access and tool-free removal or replacement;

n. The means for driving air is modular and contained within a bracket or housing, that allows all components for driving air to be connected together within a frame or housing;

o. An air intake aperture and exhaust aperture connected to the housing cooperatively coupled with the filter and means for driving air;

p. Hingable air intake aperture and hingable exhaust aperture, although independent and separate devices, may be combined with hingable room luminaire or hingable room surface and air decontamination luminaire to form a single hingable and removable front panel with latch attachment to allow access to all components, including decontamination maintenance panel for maintenance and repairs;

q. An internal chamber or duct disposed in the housing internal space defining a decontamination chamber or air decontamination chamber therebetween; and r. At least one internal decontamination source adapted to be placed, attached or mounted within the decontamination chamber, wherein the air drawn through the air intake aperture and through the decontamination chamber where comes in direct contact with decontamination source for propel and effective decontaminated by the at least one decontamination source, and wherein the air is exhausted from the decontamination chamber and expel through the air exhaust aperture directly into the room.

Room Surface and Air Decontamination Luminaire

13. The Recessed Ceiling or Surface Decontamination System of concept 12, further comprising at least one selectively operable Room Surface and Air Decontamination Luminaire is disposed on the housing, in a hinging and removable relationship to properly and effectively decontaminate air and surfaces in the area or room where the unit is mounted.

Internal Decontamination Source is UV-C/Germicidal/Ozone.

14. The Recessed Ceiling or Surface Decontamination System of concept 12, wherein the at least one internal decontamination source installed in parallel orientation with air flow through the chamber, located within the decontamination chamber is selected from a group consisting from germicidal light, ultraviolet light, ultraviolet-C light (UV-C), ozone, sonic source, and ultrasonic source or other known decontamination source.

Room Surface and Air Decontamination Source

15. The Recessed Ceiling or Surface Decontamination System of concept 12, wherein the at least one internal decontamination source associated with the Room Surface and Air Decontamination Luminaire is selected from a group consisting from germicidal light, ultraviolet light, ultraviolet-C light (UV-C), ozone, sonic source, and ultrasonic source or other known decontamination source.

Intake and Exhaust Aperture Interchangeable

16. The Recessed Ceiling or Surface Decontamination System claim 15, wherein the air intake aperture and the air exhaust aperture are interchangeable and selectively capable of simultaneously enabling reverse air flow direction, wherein the air exhaust means draw the air from the air exhaust aperture and the air intake means exhaust the air through the air intake aperture without additional modifications or altering the effectiveness of the decontamination system.

17. The ceiling-mounted decontamination unit of concept 15, further comprising one or more of a mounted indicator to provide an alert if a component fails 18. The ceiling-mounted decontamination unit of concept 15, further comprising one or strobe devices connected to the Room Surface and Air Decontamination Luminaire to provide an alert or waring that room air and surface decontamination system are active.

19. The ceiling-mounted decontamination unit of concept 16 incorporating a monitoring system for communicating the operating status of the light fixture/luminaire, internal decontamination system, and external decontamination system to an off-site location monitoring station.

20. A Room Surface and Air Decontamination Luminaire, hingable and removable, including an occupancy sensor to shut down power to unit when room is occupied in any way, a warning strobe and audible alarm to alert when surface decontamination system is active, designed to destroy pathogens on surfaces and air utilizing sources selected from a group consisting from germicidal light, ultraviolet light, ultraviolet-C light (UV-C), ozone, sonic source, and ultrasonic source or other known decontamination source.

Door Panel Switch

21. The Recessed Ceiling or Surface Decontamination has a door switch, kill switch, or power interrupting switch to disconnect power to system when intake aperture, exhaust aperture, hingable ceiling time in frame, hingable room luminaire, or hingable surface and air decontamination luminaire are opened or disengaged from the housing.

Occupancy Sensor

22. The Recessed Ceiling or Surface Decontamination System of concept 1, further comprising a room occupancy sensor or motion sensor directly attached to the hingable room surface and air decontamination luminaire for deactivating the room surface and air decontamination luminaire when room is occupied.

Self Contained Luminaire

23. Recessed Ceiling or Surface Mounted Air Decontamination System
   h. Hinged Flat Panel FULL SIZE Luminaire with Vents through lens and components installed on rear.
   i. LED Flat Panel with Vent Ducts.
   j. No Adapter or Install Apparatus.
   k. Four-Corner Cable Support.
   L. Storage Area for extra filters.

m. Fan location post decontamination to keep fans pathogen-free.

n. Constant speed

24. The components associated with the air decontamination system should accessible from below the installed unit on the ceiling grid. Access to the decontamination source, power supply connection, filer, drivers, ballasts, means for moving air, and all other components are available from below the installed unit, on the room side of the installed unit, and without moving or disengaging the air decontamination system from the installed position on the ceiling grid.

What is claimed is:

1. A ceiling-mounted decontamination unit, comprising:
   a. A housing, having a top and four walls connected to the top, each wall having a lower edge, defining an internal space between the top and four lower edges, said housing adapted to be permanently attached or mounted into a recessed or drop ceiling grid or plaster or sheetrock ceiling by securing means coupled with the housing and said housing being capable of receiving and securely holding a luminaire or an external decontamination source;
   b. At least one intake aperture and at least one exhaust aperture located between the first lower edge and the second lower edge so that the luminaire or the external decontamination source is positioned between the at least one intake aperture and the at least one exhaust aperture, said at least one intake aperture being suitable for drawing air into the internal space and said at least one exhaust aperture being suitable for expelling decontaminated air from the internal space;
   c. An internal decontamination source coupled with the top inside the internal space, defining a decontamination chamber for air flow between the internal decontamination source and the luminaire or the external decontamination source;
   d. One or more fan for driving air coupled with the housing and cooperating with the at least one intake aperture and the at least one exhaust aperture to drive air through the decontamination chamber, wherein the air is decontaminated by the internal decontamination source when the air passes through the decontamination chamber; and
   e. An electrical raceway coupled with the housing for providing electrical power to the internal decontamination source, the one or more fan for driving air, and any additional electrical components of the ceiling-mounted decontamination unit, said electrical raceway being in electric communication with the internal decontamination source and the one of more fan for driving air.

2. A ceiling-mounted decontamination unit, comprising:
   a. A housing, having a top and four walls connected to the top, each wall having a lower edge, defining an internal space between the top and four lower edges, said housing adapted to be removably or semi-permanently attached or mounted into a recessed or drop ceiling grid or plaster or sheetrock ceiling by securing means coupled with the housing and said housing being capable of receiving and securely holding a luminaire or an external decontamination source;
   b. At least one intake aperture and at least one exhaust aperture located between the first lower edge and the second lower edge so that the luminaire or the external decontamination source is positioned between the at least one intake aperture and the at least one exhaust aperture, said at least one intake aperture being suitable for drawing air from a room into the internal space and said at least one exhaust aperture being suitable for expelling decontaminated air from the internal space directly back into the room;
   c. At least one internal decontamination source coupled with the top inside the internal space, defining at least one decontamination chamber for air flow between the at least one internal decontamination source and the luminaire or the external decontamination source; and
   d. One or more fan for driving air coupled with the housing and cooperating with the at least one intake aperture and the at least one exhaust aperture to drive air through the at least one decontamination chamber, wherein the air is decontaminated by the at least one internal decontamination source when the air passes through the at least one decontamination chamber.

3. The ceiling-mounted decontamination unit of claim 2, further comprising an electrical raceway coupled with the housing for providing electrical power to the at least one internal decontamination source, the one or more fan for driving air, and any additional electrical components of the ceiling-mounted decontamination unit, said electrical raceway being in electric communication with the at least one internal decontamination source and the one of more fan for driving air.

4. A ceiling-mounted decontamination unit, comprising:
   a. A housing, having a top and four walls connected to the top, each wall having a lower edge, defining an internal space between the top and four lower edges, said housing adapted to be removably or semi-permanently attached or mounted into a recessed or drop ceiling grid or plaster or sheetrock ceiling by securing means coupled with the housing;
   b. a luminaire or an external decontamination source attached to the housing along a first lower edge and having at least one latch interlocking with a cooperating at least one latch provision coupled with a second lower edge opposite to the first lower edge so as to enable selective downward opening of the luminaire, the external decontamination source when the at least one latch is disengaged to provide access to the internal space;
   c. At least one intake aperture and at least one exhaust aperture located between the first lower edge and the second lower edge so that the luminaire or the external decontamination source is positioned between the at least one intake aperture and the at least one exhaust aperture, said at least one intake aperture being suitable for drawing air from a room into the internal space and said at least one exhaust aperture being suitable for expelling decontaminated air from the internal space directly back into the room;
   d. At least one internal decontamination source coupled with the top inside the internal space, defining at least one decontamination chamber for air flow between the at least one internal decontamination source and the luminaire or the external decontamination source; and
   e. One or more fan for driving air coupled with the housing and cooperating with the at least one intake aperture and the at least one exhaust aperture to drive air through the at least one decontamination chamber, wherein the air is decontaminated by the at least one internal decontamination source when the air passes through the at least one decontamination chamber.

5. The ceiling-mounted decontamination unit of claim 4, further comprising an electrical raceway coupled with the housing for providing electrical power to the luminaire, the external decontamination source, the at least one internal decontamination source, the one or more fan for driving air, and any additional electrical components of the ceiling-mounted decontamination unit, said electrical raceway being in electric communication with the at least one internal decontamination source and the one of more fan for driving air.

6. The ceiling-mounted decontamination unit of claim 4, further comprising at least one modular electrical connector between the luminaire or the external decontamination source, said least one modular electrical connector cooperating with a reciprocal at least one modular electrical connector disposed on the housing in the internal space.

7. The ceiling-mounted decontamination unit of claim 6, wherein the selective downward opening of the luminaire or the external decontamination source provides access to the internal space for maintenance of the at least one intake aperture, the at least one exhaust aperture, the at least one internal decontamination source, the at least one decontamination chamber, the electrical raceway, the at least one modular electrical connector, or the one or more fan for driving air without disconnecting the housing from a recessed or drop ceiling grid or plaster or sheetrock ceiling or moving the housing.

8. A ceiling-mounted decontamination unit, comprising:
   a. A housing, having a top and four walls connected to the top, each wall having a lower edge, defining an internal space between the top and four lower edges, said housing adapted to be removably or semi-permanently attached or mounted into a recessed or drop ceiling grid or plaster or sheetrock ceiling by securing means coupled with the housing;
   b. a luminaire or an external decontamination source attached to the housing along a first lower edge and having at least one latch interlocking with a cooperating at least one latch provision coupled with a second lower edge opposite to the first lower edge so as to enable selective downward opening of the luminaire or the external decontamination source when the at least one latch is disengaged to provide access to the internal space, the luminaire or the external decontamination source having at least one intake aperture and at least one exhaust aperture therein, said at least one intake aperture being suitable for drawing air from a room into the internal space and said at least one exhaust aperture being suitable for expelling decontaminated air from the internal space directly back into the room;
   c. At least one internal decontamination source coupled with the top inside the internal space, defining at least one decontamination chamber for air flow between the at least one internal decontamination source and the luminaire or the external decontamination source; and
   d. One or more fan for driving air coupled with the housing inside the internal space and cooperating with the at least one intake aperture and the at least one exhaust aperture to drive air through the at least one decontamination chamber, wherein the air is decontaminated by the at least one internal decontamination source when the air passes through the at least one decontamination chamber.

9. The ceiling-mounted decontamination unit of claim 8, further comprising an electrical raceway coupled with the housing for providing electrical power to the luminaire, the external decontamination source, the at least one internal decontamination source, the one or more fan for driving air, and any additional electrical components of the ceiling-mounted decontamination unit, said electrical raceway being in electric communication with the at least one internal decontamination source and the one of more fan for driving air.

10. A ceiling-mounted decontamination unit, comprising:
   a. A housing, having a top and four walls connected to the top, each wall having a lower edge, defining an internal space between the top and four lower edges, said housing adapted to be removably or semi-permanently attached or mounted into a recessed or drop ceiling grid or plaster or sheetrock ceiling by securing means coupled with the housing;
   b. a luminaire or an external decontamination source attached to the housing along a first lower edge and having at least one latch interlocking with a cooperating at least one latch provision coupled with a second lower edge opposite to the first lower edge so as to enable selective downward opening of the luminaire or the external decontamination source when the at least one latch is disengaged to provide access to the internal space, the luminaire or the external decontamination source having at least one intake aperture and at least one exhaust aperture therein, said at least one intake aperture being suitable for drawing air from a room into the internal space and said at least one exhaust aperture being suitable for expelling decontaminated air from the internal space directly back into the room, and the luminaire or the external decontamination source also having an interior side facing the internal space and an exterior side facing the room;
   c. At least one internal decontamination source coupled with the interior side, defining at least one decontamination chamber for air flow inside the internal space between the at least one internal decontamination source and the top; and
   d. One or more fan for driving air coupled with the luminaire or the external decontamination source and cooperating with the at least one intake aperture and the at least one exhaust aperture to drive air through the at least one decontamination chamber, wherein the air is decontaminated by the at least one internal decontamination source when the air passes through the at least one decontamination chamber.

11. The ceiling-mounted decontamination unit of claim 10, further comprising an electrical raceway coupled with the luminaire or the external decontamination source for providing electrical power to the luminaire, the external decontamination source, the at least one internal decontamination source, the one or more fan for driving air, and any additional electrical components of the ceiling-mounted decontamination unit, said electrical raceway being in electric communication with the at least one internal decontamination source and the one of more fan for driving air.

* * * * *